United States Patent
Thomas et al.

(10) Patent No.: US 12,339,245 B2
(45) Date of Patent: Jun. 24, 2025

(54) METHODS AND SYSTEMS FOR DETERMINING A TARGET GAS CONCENTRATION IN A FLUID ENVIRONMENT

(71) Applicant: H2Scan Corporation, Valencia, CA (US)

(72) Inventors: Dylan Thomas, Canyon Country, CA (US); Tim Howard, Canyon Country, CA (US)

(73) Assignee: H2Scan Corporation, Valencia, CA (US)

( * ) Notice: Subject to any disclaimer, the term of this patent is extended or adjusted under 35 U.S.C. 154(b) by 423 days.

(21) Appl. No.: 17/601,389

(22) PCT Filed: Apr. 6, 2020

(86) PCT No.: PCT/US2020/026905
§ 371 (c)(1),
(2) Date: Oct. 4, 2021

(87) PCT Pub. No.: WO2020/206438
PCT Pub. Date: Oct. 8, 2020

(65) Prior Publication Data
US 2022/0187230 A1    Jun. 16, 2022

Related U.S. Application Data

(60) Provisional application No. 62/830,182, filed on Apr. 5, 2019.

(51) Int. Cl.
*G01N 27/12* (2006.01)
*G01N 27/04* (2006.01)
*G01N 33/00* (2006.01)

(52) U.S. Cl.
CPC ......... *G01N 27/122* (2013.01); *G01N 27/046* (2013.01); *G01N 33/0004* (2013.01)

(58) Field of Classification Search
CPC ............... G01N 27/122; G01N 27/046; G01N 27/124; G01N 27/129; G01N 27/123;
(Continued)

(56) References Cited

U.S. PATENT DOCUMENTS 3,759,083 A    9/1973    Erickson et al.
8,265,881 B1   9/2012    Lakhotia et al.
(Continued)

FOREIGN PATENT DOCUMENTS

CN    1836154      9/2006
CN    108431594    8/2018
(Continued)

OTHER PUBLICATIONS

Short-Time Fourier Transform and Decision Tree-Based Pattern Recognition for Gas Identification Using Temperature Modulated Microhotplate Gas Sensors, Aixiang He, Hindawi Publishing Corporation, Journal of Sensors, vol. 2016, Article ID 7603931, Published Feb. 28, 2016. (Year: 2016).*

(Continued)

*Primary Examiner* — Catherine T. Rastovski
*Assistant Examiner* — Lal C Mang
(74) *Attorney, Agent, or Firm* — Jeffrey G. Sheldon; Cislo & Thomas LLP

(57) ABSTRACT

A system and method of determining a target gas concentrations in a fluid environment using a gas sensor that improves the efficiency and accuracy of the gas sensor's measurements by taking measurements of electrical characteristics of the gas sensor at different temperatures, taking measurements during a transition between a first temperature and a second temperature, taking more frequent mea- (Continued)

surements, detecting when the gas sensor has reached equilibrium, using multiple sensors, accounting for offsets and drifts, reducing the time the sensor is not live, using various algorithms, or any combination thereof.

26 Claims, 15 Drawing Sheets

(58) Field of Classification Search
CPC ............ G01N 33/0004; G01N 33/005; G01N 33/0006; G01N 33/0016; G01N 33/0073
See application file for complete search history.

(56) References Cited

U.S. PATENT DOCUMENTS

| | | | |
|---|---|---|---|
| 9,459,223 B1* | 10/2016 | Alqahtani | G01N 33/0036 |
| 2004/0193379 A1 | 9/2004 | Lillis et al. | |
| 2004/0261500 A1 | 12/2004 | Ng et al. | |
| 2005/0182574 A1 | 8/2005 | Sano et al. | |
| 2009/0133472 A1 | 5/2009 | Tada et al. | |
| 2009/0238752 A1 | 9/2009 | Galloway et al. | |
| 2012/0227466 A1* | 9/2012 | Medlin | G01N 27/129 73/31.06 |
| 2013/0086975 A1* | 4/2013 | Lakhotia | G01N 33/0059 73/19.1 |
| 2013/0217140 A1* | 8/2013 | Fietzek | G01N 33/0004 436/141 |
| 2016/0123930 A1* | 5/2016 | Noyce | G01N 29/2437 422/69 |
| 2016/0238578 A1* | 8/2016 | Lakhotia | G01N 27/12 |
| 2018/0238822 A1* | 8/2018 | Chen | G01N 27/127 |
| 2018/0238882 A1 | 8/2018 | Tsionsky et al. | |
| 2020/0333308 A1 | 10/2020 | Billat et al. | |

FOREIGN PATENT DOCUMENTS

| | | |
|---|---|---|
| DE | 19628033 | 11/1997 |
| EP | 0829718 | 3/1998 |
| EP | 2762877 | 8/2014 |
| JP | 03-123842 | 5/1991 |
| JP | 58-189547 | 10/2008 |
| JP | 2017156293 | 9/2017 |
| JP | 2021-509955 | 4/2021 |
| WO | WO2007117156 A1 | 10/2007 |
| WO | WO2017202571 | 11/2017 |
| WO | WO2018201201 A1 | 11/2018 |
| WO | 2019135004 | 7/2019 |

OTHER PUBLICATIONS

NPL 1 continued: https://downloads.hindawi.com/journals/js/2016/7603931.pdf?_gl=1*td0wgc*_ga*NDIzODY2ODIzLjE3MTA1MjM5NzI.*ga_NF5QFMJT5V*MTcxMDUyMzk3Mi4xLjAuMTcxMDUyMzk3OS41My4wLjA.&_ga=2.88835675.1743128106.1710523972-423866823.1710523972 (Year: 2016).*

Ma, et al., A novel wireless gas sensor based on LTCC technology. Sensors and Actuators B., Aug. 13, 2016. vol. 239 DOI: 10.1016/j.snb.2016.08.073; abstract; p. 715, figure 6.

He A, et al. Short-Time Fourier Transform and Decision Tree-Based Pattern Recognition for Gas Identification Using Temperature Modulated Microhotplate Gas Snsors, Journal of Sensors, 2016. DOI: 10.1155/2016/760931; abstract; p. [0025], [0031]; figures 2(1) and 3.

Maclay, et al., "Use of Time-dependent Chemical Sensor Signals for Selective Identification," Sensors and Actuators, 20 (1989), 277-285, 9 pages.

Hughes, R.C., et al, "Chemical Microsensors," Science, vol. 245, Oct. 4, 1991, pp. 74-80.

Hughes, R.C., et al., "Thin-Film Palladium and Silver Alloys and Layers for Metal-Insulator-Semiconductor Sensors," J. Appl. Phys., vol. 62, No. 3, Aug. 1, 1987, pp. 1074-1083.

Löfdahl, Mikael, et. al., Difference in Hydrogen Sensitivity Between Pt and Pd Field-Effect Devices, J. Appl. Phys., vol. 91, No. 7, Apr. 1, 2002, pp. 4275-4280.

Indian Patent Application No. 848/MUMNP/2014. Hearing Notice dated Jan. 2, 2023. 3 pages.

Korean Patent Application No. 10-2021-7035357. Office Action dated Oct. 27, 2023 and English Translation. 13 pages.

Indian Patent Application No. 202117049798. "First Examination Report" dated Jul. 18, 2022. 7 pages.

He et al. "Short-Time Fourier Transform and Decision Tree-Based Pattern Recognition for Gas Identification Using Temperature Modulated Microhotplate Gas Sensors". Hindawi Publishing Corporation. Journal of Sensors, vol. 2016, Article ID 7603931, 13 pages. Feb. 8, 2016.

Taiwan Application No. 109111431. First Office Action dated Oct. 4, 2023. 25 pages.

European Patent Application No. 20782033.3. "Communication pursuant to Rules 70(2) and 70a(2) EPC" dated Oct. 5, 2022. 75 pages.

Indian Patent Application No. 202117049798. Hearing Notice dated May 13, 2024. 3 pages.

Taiwanese Patent Application No. 113118700. Office Action dated Sep. 12, 2024 and machine translation. 14 pages.

European Patent Application No. 25157529.6 Extended European Search Report dated Mar. 13, 2025. 7 pages.

* cited by examiner

METHODS AND SYSTEMS FOR DETERMINING A TARGET GAS CONCENTRATION IN A FLUID ENVIRONMENT

CROSS-REFERENCE TO RELATED APPLICATIONS

This patent application national phase application of PCT Patent Application No. PCT/US2020/026905, filed Apr. 6, 2020, which claims the benefit of U.S. Provisional Patent Application Ser. No. 62/830,182, entitled "METHODS AND SYSTEMS FOR DETERMINING A TARGET GAS CONCENTRATION IN A FLUID ENVIRONMENT," filed Apr. 5, 2019, which applications are incorporated in their entirety here by this reference.

TECHNICAL FIELD

This invention relates to systems and methods for determining gas concentrations in a fluid environment.

BACKGROUND

Numerous gas sensors are known in the art. Gas concentrations can be measured by observing the changes in electrical properties (such as current, voltage, capacitance, resistance, and the like) of the sensors. Thus, resistive sensors, capacitive sensors, and semiconductor sensors such as transistor, or diode sensors are known in the art.

As a particular example, thin-film PdNi alloy resistors have been used to detect gases such as hydrogen and measure its concentration. Hydrogen is soluble in PdNi and the resistivity of the thin-film PdNi alloy increases upon exposure to hydrogen and the amount of increase is proportional to the square root of hydrogen partial pressure. Some gas sensors, such as one that has a PdNi lattice, may have increased resistance or changed capacitance or a characteristic of the semiconductor as concentration of $H_2$ increases. For example, resistance may increase linearly in proportion to the square root of the hydrogen in a PdNi lattice, which in turn is related to gaseous $H_2$ pressure as described by Sievert's law.

For a given application, a gas sensing system can be designed to detect the pressure of a target gas, for example, $H_2$. In addition to the target gas pressure, however, there may be factors that can influence a gas sensor's measurements. For example, temperature of the gas sensor may influence measurements. To address this issue, a heater may be used to maintain the gas sensor within a desired temperature range. In addition to temperature, other factors may influence gas sensor measurements, such as a bias voltage applied to the gas sensor or the overall pressure of the fluid environment. These measurements are also prone to errors due to baseline drift associated with aging and the presence of unwanted gases and shifts in the sensor characteristics. For example, if a table was generated associating partial pressures of hydrogen with resistances of the sensor (given that the resistances are associated with the same sensor temperature), over time these associations would no longer be true due to the aforementioned examples. Measurements based on this table would thus be in error. One solution to this problem is to employ a system that performs calibrations and performs gas measurements at two different temperatures.

Non-target gases, such as $O_2$, may also influence a gas sensor's measurements. The presence of non-target gases may influence or interfere with target gas measurements in at least two ways. First, because the sensor is responding to both a target and a non-target gas, the sensor reading may be too high or too low. In this respect, the influence of the non-target gas may be thought of as an offset to the target gas reading. Second, the presence of a non-target gas can alter the way a sensor measures a target gas. For example, non-target gases can occupy receptor sites inside or on the surface of the lattice. This leaves less available receptor sites, thereby making the sensor less sensitive to the target-gas. As another example, in a PdNi gas sensor, the presence of oxygen in the lattice may affect the resistive or capacitive characteristics of the sensor. Thus, an oxygen-permeated lattice may respond to the presence of hydrogen in a different way than if the lattice was not permeated with oxygen. When oxygen permeates the lattice adsorption of hydrogen results in the formation of molecules such as $H_2O$, OH, etc. These molecules may, by themselves, influence the resistive or capacitive characteristics of the gas sensor.

One attempted solution for reducing the influence of non-target gases may be to use a blocking coating on a gas sensor to filter such non-target gases. However, such a filter may reduce a gas sensor's sensitivity or response time. Another attempted solution may be to use multiple gas sensors to specifically detect non-target gases to determine and account for concentration information for non-target gases. However, such a solution may be expensive and/or introduce additional system complexity. Yet another attempted solution is to simply limit gas-sensing applications to ones that do not include interfering gases. A solution to the drift problem is to repeatedly recalibrate a drifting sensor manually.

For the foregoing reasons there is a need for methods and systems for accurately and efficiently measuring gas concentrations with advantages such as, but not limited to, reducing or eliminating the need for calibrations requiring reference gases, as well as maintaining or exceeding accuracy, response time, and precision of requirements for hydrogen measuring and hydrogen monitoring applications, all while providing a continuous or minimally interrupted reading.

SUMMARY

The present invention is directed to methods and systems that can efficiently and accurately measure gas concentrations or gas content in a fluid environment. The methods and systems comprise the use of devices and techniques that take measurements at different temperatures, take measurements during a transition between a first temperature and a second temperature, take more frequent measurements, detect when the gas sensor has reached equilibrium, use multiple sensors, account for offsets and drifts, reduce the time the sensor is not live, use algorithms, or any combination thereof. As a result, the system and method of the present application reduces or eliminates the need for periodic calibration in some hydrogen measurement and hydrogen monitoring applications, physically achieves accuracy, response time, and precision of current hydrogen measuring and monitoring products, and reduces or eliminates gaps in hydrogen reporting.

DESCRIPTION

The detailed description set forth below in connection with the appended drawings is intended as a description of presently-preferred embodiments of the invention and is not intended to represent the only forms in which the present invention may be constructed or utilized. The description sets forth the functions and the sequence of steps for constructing and operating the invention in connection with the illustrated embodiments. It is to be understood, however, that the same or equivalent functions and sequences may be accomplished by different embodiments that are also intended to be encompassed within the spirit and scope of the invention.

Figure 1:
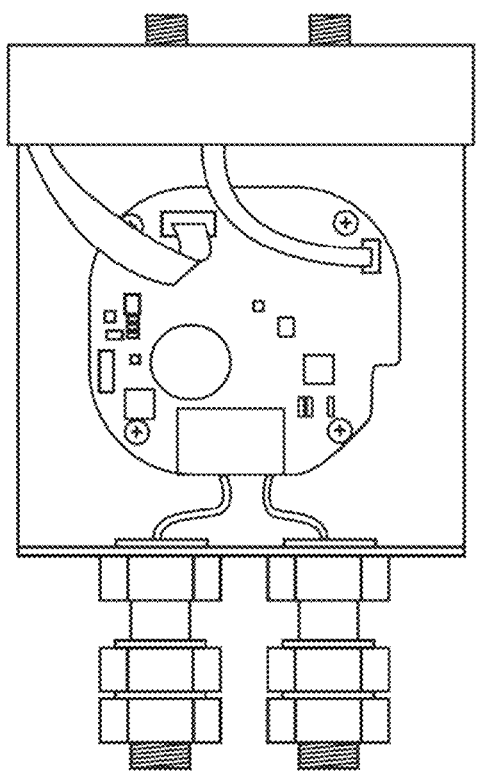
FIG. 1 is an embodiment of the present invention.

The present invention is directed towards systems and methods for the determination of a target gas concentration in a fluid environment, such as the concentration of hydrogen in a fluid environment by measuring changes in electrical properties of a gas sensor at at least two different temperatures as disclosed in U.S. Provisional Application No. 62/830,182, filed Apr. 5, 2019, which application is incorporated in its entirety here by this reference. Measuring electrical properties of a gas sensor at two different temperatures can be used to calculate the gas concentration or can be used to calibrate or correct the measurement of electrical properties of a gas sensor at a single temperature. Preferably, the systems and methods can determine gas concentrations continuously without compromising accuracy. By way of example only, a system may comprise a gas sensor as described in U.S. patent application Ser. No. 14/624,400, filed Feb. 17, 2015, which application is incorporated in its entirety here by this reference. With reference to FIG. 1, in some embodiments, the sensor tube comprises a gas sensor, which in turn comprises a die having a gas resistor, a temperature resistor, and a heater, and two gas sensors are connected to each electronics board set. The gas resistor may be a hydrogen resistor. Methods for measuring gas concentrations include a variety of techniques as described below that can be used alone or in any combination thereof to improve the accuracy of measuring gas concentrations in a fluid environment.

Two-Temperature Transient Gas Calculation Feature

One method for improving the measurement of gas concentrations in a fluid environment is to monitor a system response (how the electrical characteristics of the sensor (output) change as a function of the sensor temperature and environmental conditions (input)) by taking dynamic measurements of electrical properties (such as current, voltage, capacitance, resistance, and the like) of the gas sensor while the gas sensor is changing between two different temperatures. This two-temperature operation comprises the gas sensor being at a first temperature for a first period, transitioning to a second temperature for a second period (first transition period), being at the second temperature for a third period, and transitioning back to the first temperature for a fourth period (second transition period).

Alternatively, the gas sensor can transition to a third temperature for the fourth period of time (second transition period). The third temperature can be the same as the first temperature, or the third temperature can be different from the first temperature. Preferably, if the second temperature is a rise in temperature from the first temperature, then the third temperature is a fall in temperature. Conversely, if the second temperature is a fall in temperature from the first temperature, then the third temperature can be a rise in temperature from the second temperature. Thus, the change in temperature can follow a waveform, although the magnitudes and period need not be the same.

During the transition periods the electrical properties of the gas sensor are also in a transient state, referred to as a transient electrical response, or simply transient response. For example, the gas sensor may have a transient resistive response to the changing temperature, which can be analyzed to calculate a live hydrogen reading, even during the unstable transient response. This can be done by analyzing the magnitude and/or phase of the response. A system response can include transient responses or can also be responses that do not have transients, such as, for example, the immediate change in resistance of the Pd sensor due to the change in temperature, as any resistor changes resistance with temperature. This can also create an instability in the Pd sensor if it contains hydrogen, and then the hydrogen must slowly move into or out of the lattice to a new equilibrium, which has a secondary, time-dependent effect.

The transient electrical response can be heavily dependent on the coating on the die, specifically, the hydrogen resistor. Multiple coatings/passivation layers are used on different elements of the die, such as between the palladium-nickel lattice and the environment. So, the coating is chosen with a permeability to hydrogen such that the transient response can more easily be used to calculate hydrogen concentrations. The coating interferes with the movement of hydrogen from the measurand into the sensor or from the sensor out to the measurand, so the coating adds a delay (i.e., adds a time constant) and affects the transient response. The thickness of the coating, the density of the coating, and a number of other parameters that are either loosely or tightly controlled affect that time constant. The delay or variation in transit time can be used to help identify the presence or lack of hydrogen. For example, if hydrogen is present there can be an overshoot or undershoot in the step responses of the hydrogen sensor with a change in die temperature. Because of the hydrogen equilibrium, the balance between the sensor element (e.g., the palladium nickel sensor) and the surrounding hydrogen can be disrupted, and for the system to reach equilibrium (i.e. when the measurements are stable) can take time. In other words, there is an equilibrium resistance or steady-state behavior (e.g., the resistance at which the gas sensor will reach given enough time, assuming the partial pressure of hydrogen and the gas sensor temperature remain constant) in the lattice that can be reached, and it is a function of the partial pressure of hydrogen in the surrounding environment. Changes in the partial pressure of hydrogen in the environment are not instantaneously translated to the lattice, which will take time to reach a new equilibrium based on things like sensor temperature and permittivity of the coating. This time can be several minutes to several hours. The time the system takes to reach equilibrium can be controlled and can be used advantageously in measurement as well as classification of the environment. For example, the more hydrogen in the sensor, the longer the time to reach equilibrium. By calibrating transient responses to known hydrogen concentrations, a model can be developed (such as the sinusoidal model described herein) to measure hydrogen as a function of the measured transient response.

Repeating Thermal Waveform Feature

Rather than simply changing the temperature of the sensor from a first temperature to a second temperature, the temperature of the gas sensor is kept at a constant state of change. Preferably, the temperature of the gas sensor can be repeatedly changing in a pattern referred to as a repeating thermal waveform. As such, the electrical characteristics of the gas sensor can be in a constant state of system response to the repeating thermal waveform, such as a sinusoid. By constantly monitoring and measuring the transient responses, the magnitude and/or phase of the transient responses using a short-time Fourier transform (STFT) or Wavelet analysis can be measured. Because the concentration of hydrogen affects the transient response, the frequency response can be used to measure hydrogen. This frequency response comprises a magnitude-frequency response and a phase-frequency response. Several calibration points relating magnitude, phase, or both, of the frequency response to hydrogen concentration can be used to create a table with an interpolation or regression function. The magnitude-frequency response is the amplitudes of the spectrum of frequencies associated with the electrical characteristic of the response to the excitation. The phase-frequency response is the phases of the spectrum of frequencies associated with the electrical characteristics of the response to the excitation. By way of example only, the spectrum can be generated by recording data of the electrical characteristics of the response by sampling said data at some rate (sample frequency) for a certain duration defined by the total number of samples (window length), and using the fast Fourier transform (FFT) algorithm to generate the discrete Fourier transform (DFT). The process of performing a Fourier transform on the short segment in time of the signal is called the short-time Fourier transform (STFT). The sample frequency and window length can be chosen based on the desired bandwidth, resolution in the spectrum, delay in the processing, etc.

In traditional multi-temperature sensors, transitioning from one temperature to another causes disruptive transient responses such that the hydrogen measurement for a period of time following the transition is inaccurate. It is very difficult to calculate a factor of hydrogen concentrate with disruptive transient responses. In a system using a repeating thermal waveform approach, the system is constantly in a state of known and controlled thermal transient response, and therefore, the system can be characterized because of the nature of the repeating thermal waveform. The system can be nonlinear, but when modulated with a repeating thermal waveform to excite the system, the magnitude and phase delay of the transient response can be associated with a concentration of hydrogen.

Figure 4A:
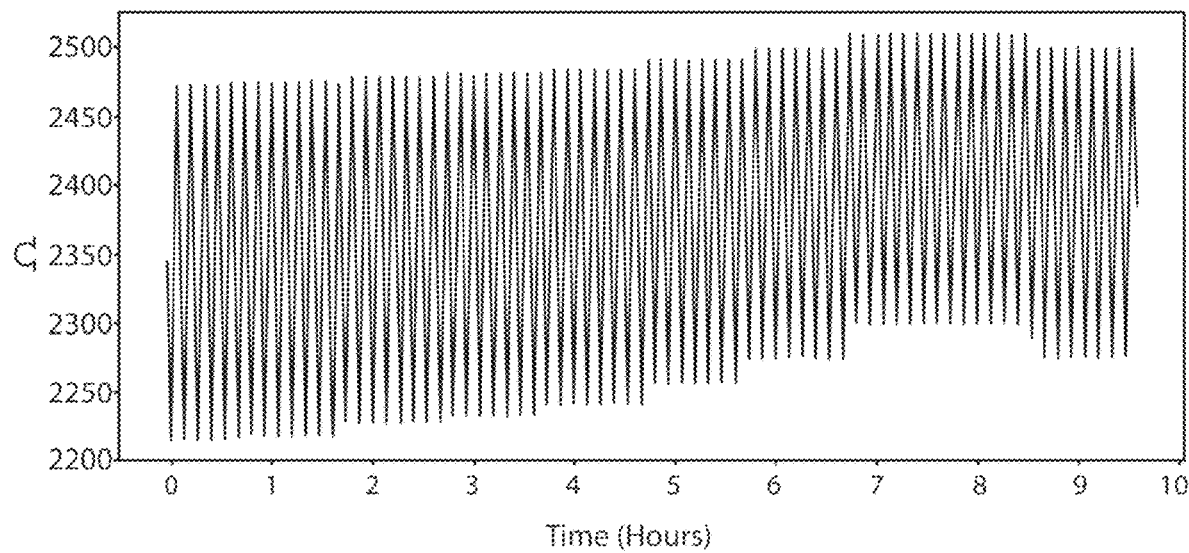
FIG. 4A shows the resistance measurement of a gas sensor exposed to multiple hydrogen gas concentrations, wherein the temperature of the resistive sensing element is modulated by a sinusoid throughout the test.

Preferably, a sine wave excitation has a single frequency making characterization of the system response in the frequency domain mathematically simpler than that of other repeating waveforms that comprise multiple frequencies. The system response to a thermal sine wave has been observed to be nonlinear, so the response contains multiple frequencies. A method of using multiple sine wave frequencies in the excitation is discussed later, but the frequencies associated with each sine wave must be carefully chosen. Having a system response comprising multiple frequencies from a single frequency excitation is still preferable to a system response to an excitation having multiple frequencies as each frequency component of the excitation will produce multiple frequency responses at the output, resulting in a complex mix of frequencies in the response. For example, a repeating waveform that induces step changes in temperature would result in a system response containing theoretically infinite sine waves, complicating the model implemented to calculated hydrogen as a function of the response. An example of the resistive response of a gas sensor being excited by a thermal sine wave in multiple hydrogen concentrations is shown in FIG. 4A. In this example, the period of the sine wave is 8 minutes, and the amplitude of the thermal waveform ranges from 50° C. to 150° C. The hydrogen concentrations shown in FIG. 4A-4D are volumetric concentrations at 1 atmosphere absolute with a background gas of nitrogen.

Figure 4B:
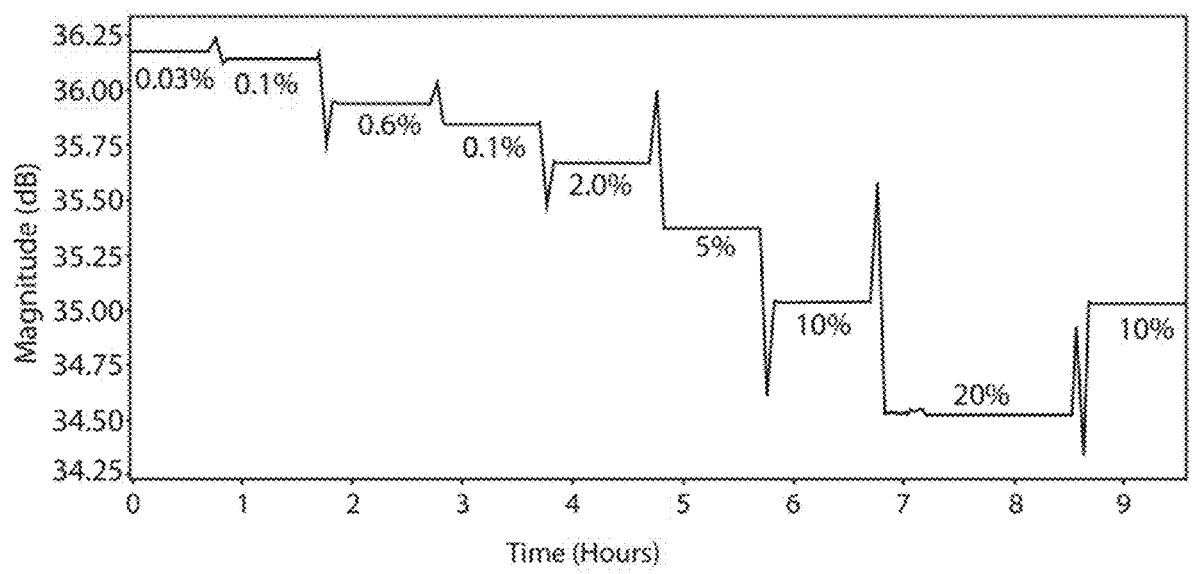
FIG. 4B shows the magnitude-frequency response associated with the resistance measurement from FIG. 4A.
Figure 4C:
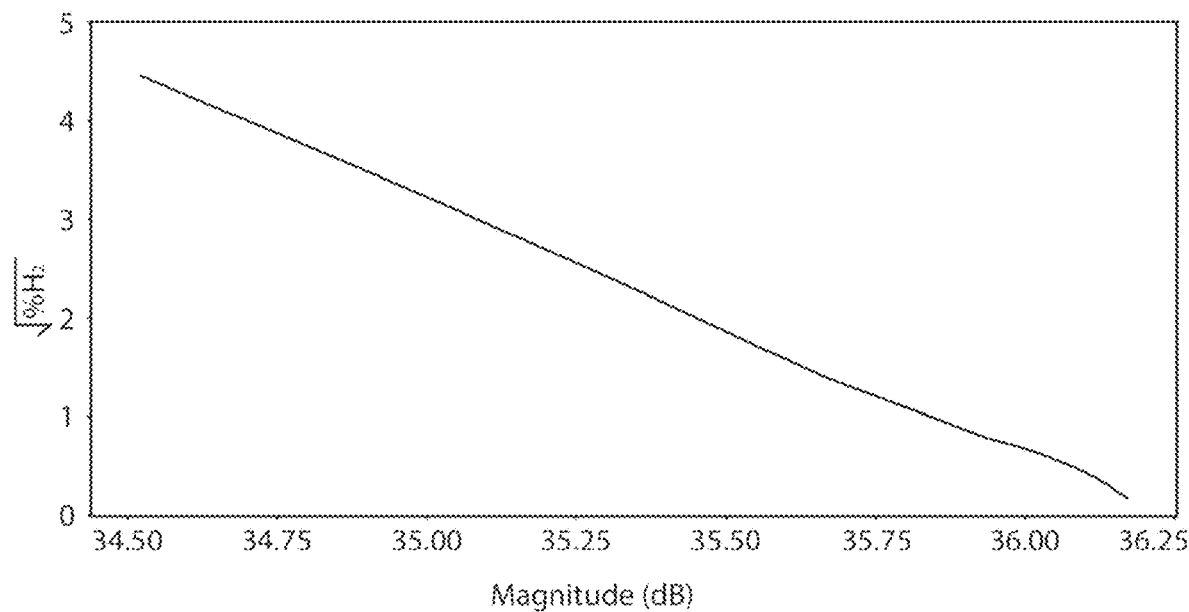
FIG. 4C shows the hydrogen as a function of the magnitude-frequency response from FIG. 4B.
Figure 4D:
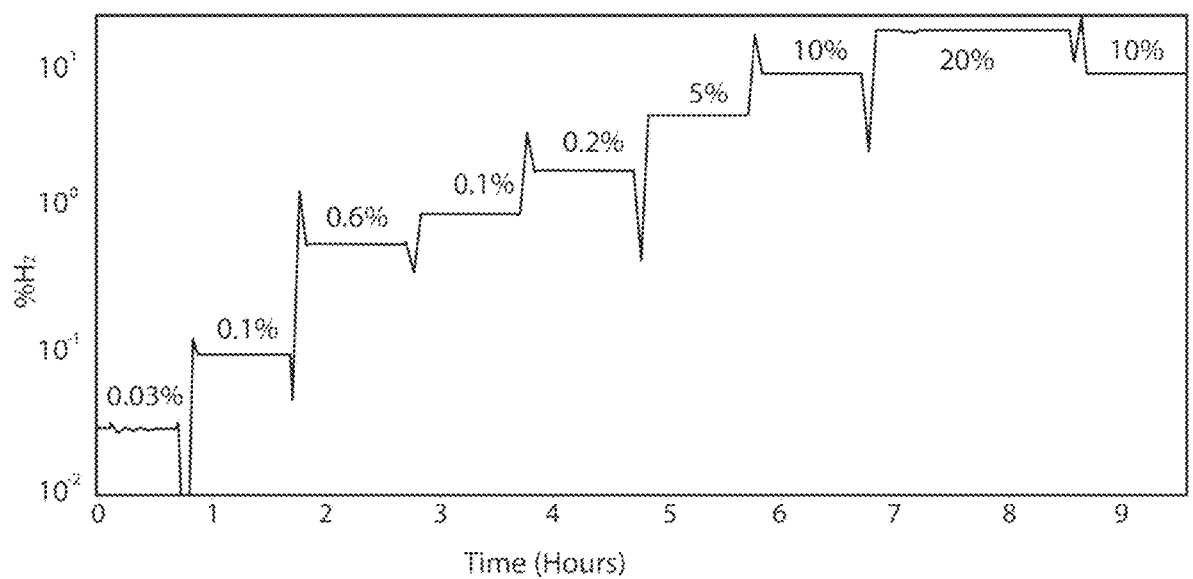
FIG. 4D shows the hydrogen concentration calculated on the data from FIG. 4B using the calibration table in FIG. 4C.

A model that utilizes a calibration table based on the system response can be created to benefit from the advantage of baseline drift removal of a multi-temperature system without the negative downtime aspect where hydrogen cannot be accurately calculated during the transients that result from the temperature transitions (or at least it is very difficult to do so). For example, by using a STFT of the transient response with a window length equal to the number of samples contained in one period of the repeating thermal waveform, and in this example, the sine wave (8 minutes), the magnitude associated with the fundamental frequency of the excitation can be measured over time. FIG. 4B shows an example of this calculation based on the transient response, wherein the transient response is a resistive response shown from FIG. 4A. A transfer function or calibration table can then be created associating gas concentrations with the frequency response (such as magnitude-frequency response and/or phase-frequency response). FIG. 4C shows the calibration table for hydrogen generated based on the magnitude-frequency response data from FIG. 4B. Using this model (FIG. 4C), the data from FIG. 4B can be used to generate a hydrogen reading. This is shown in FIG. 4D.

Figure 4E:
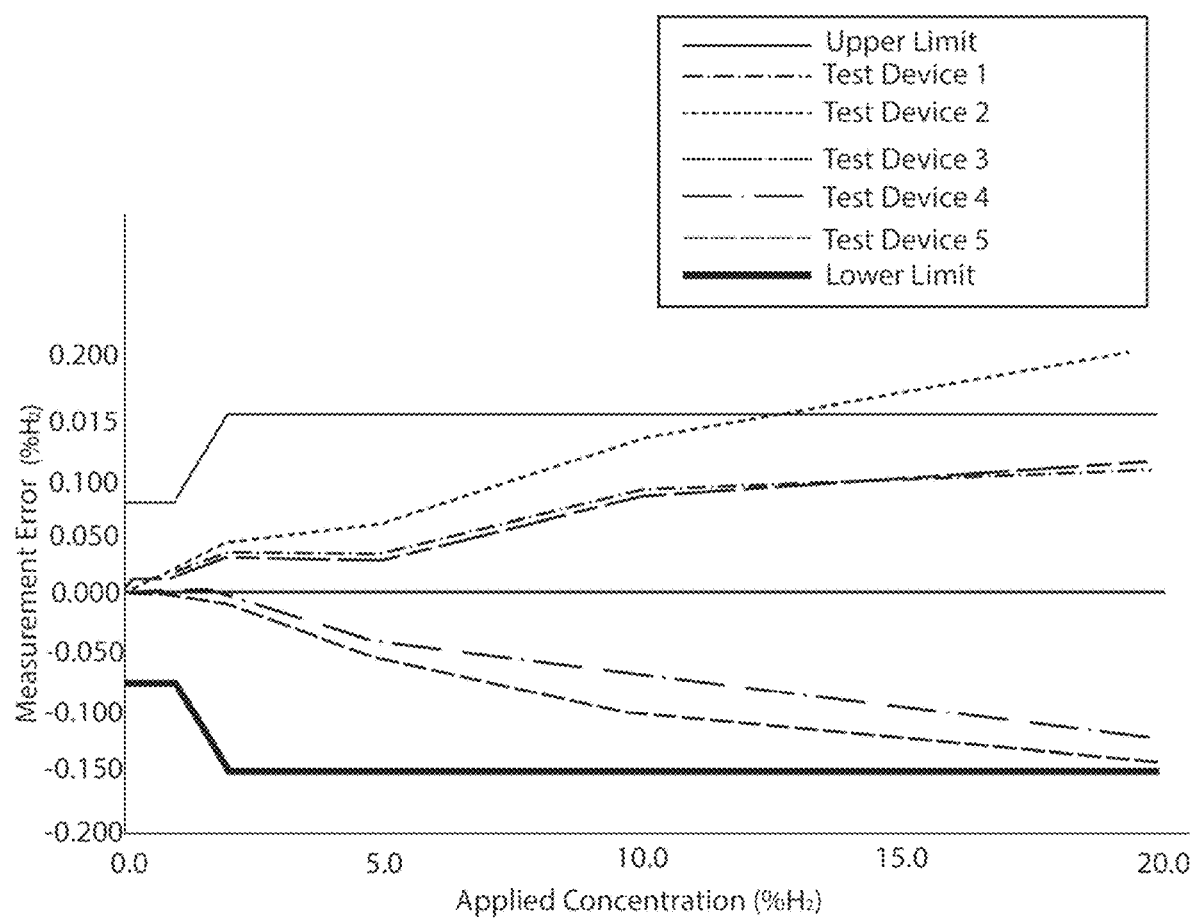
FIG. 4E shows measurement accuracy across hydrogen concentration using the thermal sinusoid method of operation shown in FIGS. 4A and 4B.

The long-term accuracy of this model can be affected if the basic system response changes. For example, foreign particulates depositing on the sensor will slow the response time, effectively changing the characteristics of the sensor. Without some way to compensate for this, the accuracy of the hydrogen reading will degrade. (See the reduced accuracy across multiple hydrogen concentrations shown in FIG. 4E.) Additionally, while there are no gaps in the hydrogen calculation due to temperature transitions, changes in hydrogen concentration that share frequency components with the fundamental frequency of the excitation affects the hydrogen calculation causing unwanted spiking in the reading. As such, when these transitions occur it may be beneficial to add additional filtering and/or other signal processing techniques such as masking the hydrogen reading until the environment stabilizes to minimize or eliminate these spikes. This effect can be observed in FIG. 4D where large spikes in the hydrogen reading can be seen as the applied hydrogen concentration is transitioned from one value to another. Additional filtering and signal processing (including masking) can be used to minimize or eliminate these spikes.

There are several approaches to correcting a change in the system response (i.e. the change in time constant) for single-sensor applications using this model. One method would be for an end-user to apply a known partial pressure of the gas (e.g., hydrogen) to the sensor, allow the device to generate some frequency response, and use this data to mathematically apply a correction to the existing frequency response calibration table. This could be repeated with additional known partial pressures of hydrogen for more accuracy. The assumption is this manual calibration would be performed less often than a single-temperature sensor to maintain hydrogen measurement performance. Another method would be to allow the device, either automatically or triggered externally, to switch to the two-temperature operation method. With this method, the accurate hydrogen reading could be captured. The device would then switch back to the thermal repeating waveform, acquire the new frequency response, and mathematically apply a correction to the existing frequency response calibration table. One assumption is the partial pressure of hydrogen to which the sensor is exposed is constant throughout this process. Another assumption is that this process is performed sparingly, and in some applications would provide preferable performance than sensors utilizing only the two-temperature method. While there may still be gaps in the hydrogen reading during the switch to the two-temperature operation method, these gaps would be infrequent compared to the two-temperature method of operation, or could be triggered when there is an acceptable time to have a gap in the hydrogen reading.

There are several methods of reducing or removing the effects of hydrogen transitions containing frequency components in the sensor response. As discussed previously, these shared frequency components cause large errors in the hydrogen calculation (shown in FIG. 4D) when using the magnitude-frequency response calibration table (FIG. 4C). One approach to mitigate this effect would be to simply mask the final hydrogen calculation if a large change in the hydrogen calculation is detected. The downside is that there would be gaps in the reading, especially at times where the partial pressure of hydrogen around the sensor is more dynamic. An alternative approach is to modulate the temperature of the sensor with multiple sine waves at specifically targeted frequencies, amplitudes, and phases. The final repeating thermal waveform is comprised of the superposition of each sine wave, meaning that said waveform is defined as the sum of sine waves, wherein each sine wave can be described by its amplitude, frequency, and phase. The system response to this waveform is comprised of the superposition of the system responses (output) to each sine wave composing the thermal waveform (input). If the frequencies of the thermal waveform input are sufficiently separated (meaning there are waveforms with low frequencies and waveforms of high frequencies), the output corresponding to each input frequency can be differentiated using common signal filtering techniques such as bandpass or notch filtering. To calculate hydrogen, each frequency has a corresponding frequency response calibration table. Lower frequency excitations were found in experimentation to have better resolution in hydrogen measurement, but shared more frequency components with hydrogen transitions, resulting in larger error during transitions. If multiple frequencies are used, the device can switch to using the data from the higher frequency excitation when a transition is detected by analyzing the stability of the frequency response of the lower frequency excitation. When the system is determined to be stable again, the device would switch back to using the data from the lower frequency excitation.

A downside of using multiple excitation frequencies in the thermal repeating waveform is the total energy of the system response must be conserved and shared across all resulting frequencies. The resulting frequency response corresponding to each frequency contains only a fraction of the signal energy of the frequency response of a single frequency (single sine wave) excitation. This reduces the signal-to-noise ratio (SNR) of the final hydrogen calculation. The signal energy can be increased by increasing the temperature variation (amplitude, or maximum and minimum temperature) of the thermal excitation. However, this is limited by physical factors (maximum temperature of materials, environment temperature, etc.).

By way of example only, the temperature variation may range from about 30 degrees Celsius to about 180 degrees Celsius. Preferably, the temperature variation ranges from 35 degrees Celsius to about 180 degrees Celsius. More preferably, the temperature variation ranges from 40 degrees Celsius to about 180 degrees Celsius. Through experimentation, it was found that the larger the variation in temperature (sinusoid amplitude), the higher the sensitivity to hydrogen using the magnitude-frequency response. This made it easier to differentiate partial pressures of hydrogen and resulted in a lower noise in the final calculation. However, because the sensor response to hydrogen is a function of temperature (the time constant of the system decreases as temperature increases), the system response becomes distorted. That is, the phase of the resistance to a constant applied hydrogen as the sensor is excited using the thermal sinusoid is not constant. The phase delay increases during the trough of the sinusoid (temperature is at the lowest value) and the phase delay decreases during the peak of the sinusoid (temperature is at the highest value). Additionally, the sensitivity of the sensor is a function of sensor temperature. The result of these effects is a distortion of the thermal sinusoid used for excitation, comprised of multiple harmonics in the resistive response.

The system may comprise a control loop and a feedback loop to control the temperature cycle. With the sinusoidal method the control loop is constantly tracking a time wave in the shape of a sinusoid. A temperature sensor measures the temperature of the die, and the temperature measurement is fed into a digital control loop. The heater can be adjusted so that the correct heat is outputted to achieve the desired temperature of the gas sensor. The heater can be controlled with a controller to use a constant transient, so any waveform can be used, including sawtooth, square wave, or any random wave form.

In some embodiments, the period of the waveform may not be fixed. In some multi-temperature embodiments, the repeating wave form does not have a fixed period. In some dual-temperature embodiments, the repeating waveform may have a fixed period, or it may not. In some embodiments, the amplitude, the phase, the wave shape, and the period may not be consistent over time. While the sinusoid has some uses, different tools for analyzing the response can be used if the system is driven from the heater and the gaseous environment that the hydrogen sensor is exposed to is measured.

In linear systems, when excited with one frequency the output contains only the same single frequency. Since the system of the present application is nonlinear, one frequency in results in multiple frequencies out (response). So, the present invention utilizes a pure sine wave to induce the hydrogen sensor's response, which will be different in amplitude, phase and can contain multiple frequencies of low amplitude or power but said changes will be diagnostic for hydrogen concentration. But the fundamental frequency of the hydrogen sensor is going to follow the frequency of the temperature change (system excitation) and its amplitude should be related to that original wave form, the driving wave form. Since the system is nonlinear, harmonics at higher frequencies will also appear, but the fundamental frequency will match the temperature modulation's fundamental frequency (lowest frequency component). Such a system does not have gaps where gas concentrations cannot be calculated during temperature-caused transients. Thus, unlike traditional gas sensors in which it would take minutes to respond between temperatures, then wait a minute or longer before another live hydrogen reading can take place; with a sinusoidal system, gas measurements are live and can be continuous as the sensor temperature is continuously modulated by the thermal waveform. Therefore, continuous hydrogen measurements can be taken. In other words, measurements are being taken on the order of seconds as opposed to a periodic hydrogen measurement which has gaps of an hour or more between measurements.

An important aspect is the distinction about forcing a thermal waveform on the die and observing the response of the hydrogen resistor. If there is no hydrogen present, the response of the hydrogen resistor can be a scaled replica in time and frequency of the driving waveform. There is very little shift or very little distortion. If the gas sensor is put in a hydrogen environment, then differences in the waveform are seen. Those differences are associated with the time constant of the hydrogen passing through the coating layers, or the hydrogen sensor reaching equilibrium with its environment. As the temperature of the Pd matrix changes, hydrogen is forced into or out of the lattice and through the coating. The rate of hydrogen passing through the coating and the hydrogen resistor's reaching equilibrium with its environment can be used. All these physical processes take time. Some of them are very fast, but others are within the operating frequencies being used for the measurements. The magnitude-frequency response and phase-frequency response of the sensor given some applied hydrogen is dependent on the system behavior, which also determines the time constant. A calibration table can be generated based on this information.

Having two different temperatures at which hydrogen concentration measurements can be taken allows for calculations or measurements with minimal or no drift or offset. Using a sinusoidal temperature waveform, however, allows for live and continuous reading of hydrogen concentrations with minimal or no drift given environmental circumstances previously discussed. Therefore, measurements of hydrogen concentrations can be determined in real time and measurements can be determined with minimal or no gaps due to responses to temperature transitions. In traditional sensors, reliable measurements are determined at the end of a period so as to give the system time to reach equilibrium. In such case, a means for determining whether the sensor had reached equilibrium was required. With a sinusoidal waveform, the gas sensor is no longer required to reach equilibrium before gas concentration measurements are determined.

Therefore, in some embodiments, a method of determining a target gas concentration in a fluid environment comprises exposing a gas sensor to the fluid environment, the gas sensor having an electrical characteristic that varies as a function of concentration of the target gas concentration, modulating the temperature of the gas sensor, wherein the modulation is in a form of a repeating thermal waveform that induces a system response in the electrical characteristics (e.g., a transient response), monitoring the electrical characteristics during the step of modulating the temperature of the gas sensor, and calculating the target gas concentration as a function of a frequency response of the electrical characteristic of the gas sensor. The frequency response can be a magnitude-frequency response of the electrical characteristics, a phase-frequency response of the electrical characteristics, or both magnitude-frequency response and phase-frequency response of the electrical characteristics.

Preferably, the repeating thermal waveform is a sine wave. In some embodiments, the repeating thermal waveform is generated by a single frequency sine wave excitation. In some embodiments, the repeating thermal waveform is generated by multiple superpositioned sine wave frequencies, wherein each sine wave frequency has a corresponding frequency response calibration table (e.g. magnitude-frequency response and/or phase-frequency response). The multiple sine waves comprise a first set of sine waves having a first set of frequencies, and a second set of sine waves having a second set of frequencies (wherein each set of sine waves has a frequency response calibration table, such as a magnitude-frequency response calibration table and/or phase-frequency response calibration table), wherein the first set of frequencies is lower than the second set of frequencies (i.e. the frequency values, or range of frequency values, in the first set is lower than the frequency values, or range of frequency values, of the second set), and wherein calculation of the target gas concentration is based on the frequency response (e.g. magnitude-frequency response and/or the phase-frequency response) of one of the first set of frequencies or the second set of frequencies. For example, the target gas concentration can be based on the first set of frequency responses or the second set of frequency responses. In other words, the frequency response to one set of frequencies can be filtered out. The cutoff between low frequency waves and high frequency waves can be determined to improve accuracy of the gas measurement or calculation.

A calibration table based on the system response can be generated. Preferably, the calibration table is generated by associating gas concentrations with a frequency response (e.g. a magnitude-frequency response, phase-frequency response, or both) measured using a Short Time Fourier Transform of the system response. Using this table, a hydrogen reading can be generated such that the accuracy does not degrade over time in certain environmental conditions.

In some embodiments, correcting a shift in the system response by applying a known partial pressure of the gas to the sensor, allowing the sensor to generate a second frequency response (e.g. a magnitude-frequency response, phase-frequency response, or both), and applying a correction to the calibration table based on the second frequency response.

In some embodiments, the calibration table can be corrected by allowing the sensor to generate a second frequency response; changing an operating mode of the gas sensor to operate at two temperatures; alternately controlling the temperature of the gas sensor between a first temperature and a second temperature while the gas sensor is exposed to the fluid environment, wherein the temperature of the gas sensor remains at the first temperature over a first period of time, transitions from the first temperature to the second temperature over a second period of time, and remains at the second temperature over a third period of time; monitoring the electrical characteristic of the gas sensor during the second and fourth periods of time; calculating the gas concentration as a function of the electrical characteristics; and calculating the correction based on the second frequency response and the calculated gas concentration.

Utilizing the system and methods described herein, the gas concentrations can be calculated continuously and in real time.

Equilibrium Detector Feature

In some embodiments, in order to achieve accurate gas concentration readings, the environment must be stable, and the sensor system must be at equilibrium. However, the length of time spent at constant temperature (first and third period described above) can be variable based on the equilibrium status of the sensor. Therefore, the time spent at one temperature is dependent on the system and the environment reaching equilibrium, which is unknown. Traditional systems are time-based and use multi-temperature operation for auto-calibration, and require the sensor measurements corresponding to each sensor temperature be at equilibrium in order to calculate an accurate calibration, but it is not known whether the system and environment have reached equilibrium. The multi-temperature style auto-calibration is performed generating a potential calibration for the sensor. If the environment was not at equilibrium or the sensor was not at equilibrium in response to the sensor temperature change, the calibration will be inaccurate. Thus, a determination must be made as to whether the results of the calibration make sense, and the calibration is either accepted or rejected as necessary. In other words, part or all the judgment is made after the sensor measurement data is acquired as to whether the calibration calculated from the sensor measurement data is accurate. If the calibration appears inaccurate, the sensor measurement data is not used, and the calibration must be reattempted. With this approach, there are oftentimes periods where the system has been stable for a very long time and measurements for the multi-temp equation could be taken earlier than scheduled. Other times the system was not quite stable but the temperature transition is scheduled just before equilibrium is reached, effectively wasting the attempt at acquiring the measurement. With an equilibrium detector, the post-sensor measurement data acquisition judgment factor is eliminated by first determining whether equilibrium has been reached by the system and the environment before taking measurements at one temperature and moving onto the next temperature, ensuring the calibration will be accurate and time is not wasted.

Currently, whether a system has reached equilibrium is time-based. The time allotted for the system to reach equilibrium in response to a sensor temperature change is fixed and set such that most sensors will have ample time to reach equilibrium. This fixed time is based on experimental data. However, changes in the environment can destabilize the readings, requiring more time for the system to stabilize, but this information is not used rigorously with current implementations.

The heating element of the gas sensor may drive the temperature, but the regulation for the die temperature is done from a temperature sensor on the die, and that part of the die is maintained at a particular temperature, although it may not be the same temperature as all parts or phases of the operation, but it typically goes through a particular sequence. So, while the sensor may be at one temperature for a first period of time, then go to a second temperature for a second period of time, to get a full cycle of the multi-temperature system and make a measurement, the existing program may vary the schedule of temperature periods if an instability is detected. Such instabilities may include large changes in environment temperature or large changes in measured electrical properties of the sensor, the thresholds of said parameters determined through experimentation. For example, the system may repeat the third period of time at the second temperature when the first period of time at the first temperature would normally be scheduled in order to quickly acquire the sensor measurement data associated with the second temperature condition. This may be performed so an auto-calibration can be calculated sooner rather than having to proceed through all normally scheduled periods (the fourth period of time to transition to the first temperature, then back to the first period at the first temperature, then to the second period of time transitioning to the second temperature, and then finally being able to repeat the third period of time at the second temperature). So, these control points are fixed timings in the traditional systems.

A more adaptive equilibrium detector, however, offers some unique properties, and helps eliminate the unknown timing factor. For example, an equilibrium detector can indicate the state of the hydrogen resistor. In the present invention, a PID type heater control loop is used to vary the temperature of the sensor. The equilibrium detector determines whether the gas sensor has reached equilibrium in response to the temperature change as well as the environment in which the sensor has been set has reached equilibrium. The method in which equilibrium is determined is based on physical measurements of the sensor such as the temperature, resistance, and power supplied to heat the sensor, as well as higher level information such as the hydrogen readings calculated using whatever model the sensor is using and the parameters generating said hydrogen reading within the model. These properties can be statistically analyzed and processed using techniques such as filtering or averaging, computing the variances (or related metrics), etc. These metrics can then be updated as new data is captured to produced additional metrics such as change over time (first derivative), change in change over time (second derivative), etc. Thresholds for these metrics are determined experimentally and depend on the precision requirements for the desired application.

Figure 2:
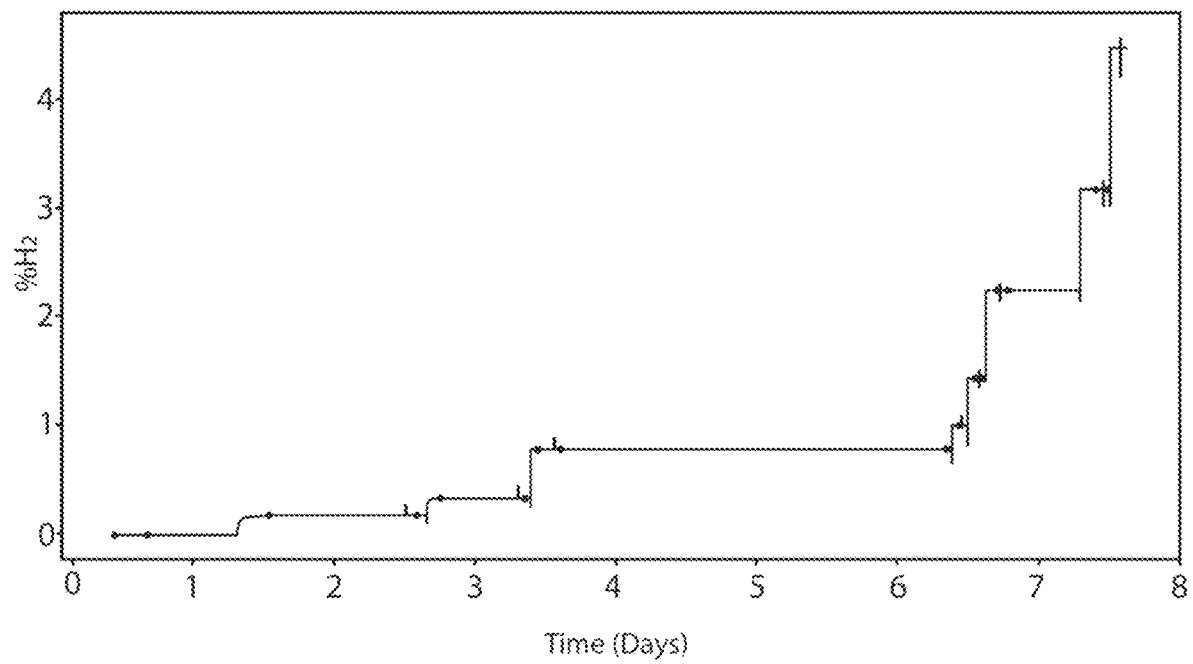
FIG. 2 shows the equilibrium detector flagging points of stability in the data.

For example, the temperature of the die of the gas sensor may be changing, or the gas concentrations of the environment may be changing. To be able to know whether the sensor is in a state of equilibrium a routine in firmware can look at the metrics described above, and based on the experimentally determined thresholds, make a determination that the sensor either is or is not in a state of equilibrium. FIG. 2 shows an example of an equilibrium detector determining when the sensor reaches equilibrium after changes in hydrogen as well as changes in sensor temperature.

Therefore, in some embodiments, a system and method of determining a target gas concentration in a fluid environment comprises exposing a gas sensor to the fluid environment, the gas sensor having an electrical characteristic that varies as a function of the target gas concentration; alternately controlling the temperature of the gas sensor between a first temperature and a second temperature while the gas sensor is exposed to the fluid environment, wherein the temperature of the gas sensor remains at the first temperature over a first period of time, transitions from the first temperature to the second temperature over a second period of time, remains at the second temperature over a third period of time, and transitions from the second temperature to a third temperature over a fourth period of time; continuously monitoring the electrical characteristic of the gas sensor during the second and fourth periods of time; and calculating the gas concentration as a function of a system response (e.g., a transient response) in the electrical characteristic of the gas sensor measured during the second and fourth periods of time when the temperature transitions between the first temperature and the second temperature. To further improve accuracy of the readings, the system can determine whether the gas sensor has reached equilibrium with an equilibrium detector.

Dual Sensor Feature

In some embodiments, rather than having one gas sensor changing temperatures, two gas sensors can be used in parallel. In some embodiments, the hydrogen readings from the dual temperature sensor are interrupted every time it switches temperature. Because it uses the multi-temp equation, its accuracy will not degrade over time, but it can have gaps in the reading due to the response to the temperature transition. Instead, a single temperature sensor (never has temperature transitions) can be used, which has a live reading (e.g., approximately 1 sample/sec reading in the current invention), but gets the true hydrogen reading from the second sensor to correct for any baseline sensor drift whenever it finishes a temperature cycle, which can take anywhere between once an hour, to once every few days. The assumption is the accuracy of the single temperature sensor will not degrade outside the specification of the application before the dual-temp/multi-temp sensor can send it a correction.

The first sensor operates at a single temperature (single-temperature sensor) such that it can constantly measure hydrogen without interruption. The second sensor calculates hydrogen using the two-temperature method (two-temperature sensor), such that it is at a first temperature for a first period, transitioning to a second temperature for a second period, being at the second temperature for a third period, and transitioning back to a third temperature for a fourth period. The third temperature can be the same temperature as the first temperature or a different temperature. Because the second sensor can account for drift over time (due to instability, oxidation, interference gases such as CO or $H_2S$, etc.) but only has intermittent but reliable hydrogen measurements, it can pass these measurements as calibrations to the first sensor. In other words, the information is fed forward from the second sensor to the first, "live" sensor, as each auto-calibration completes.

Figure 3A:
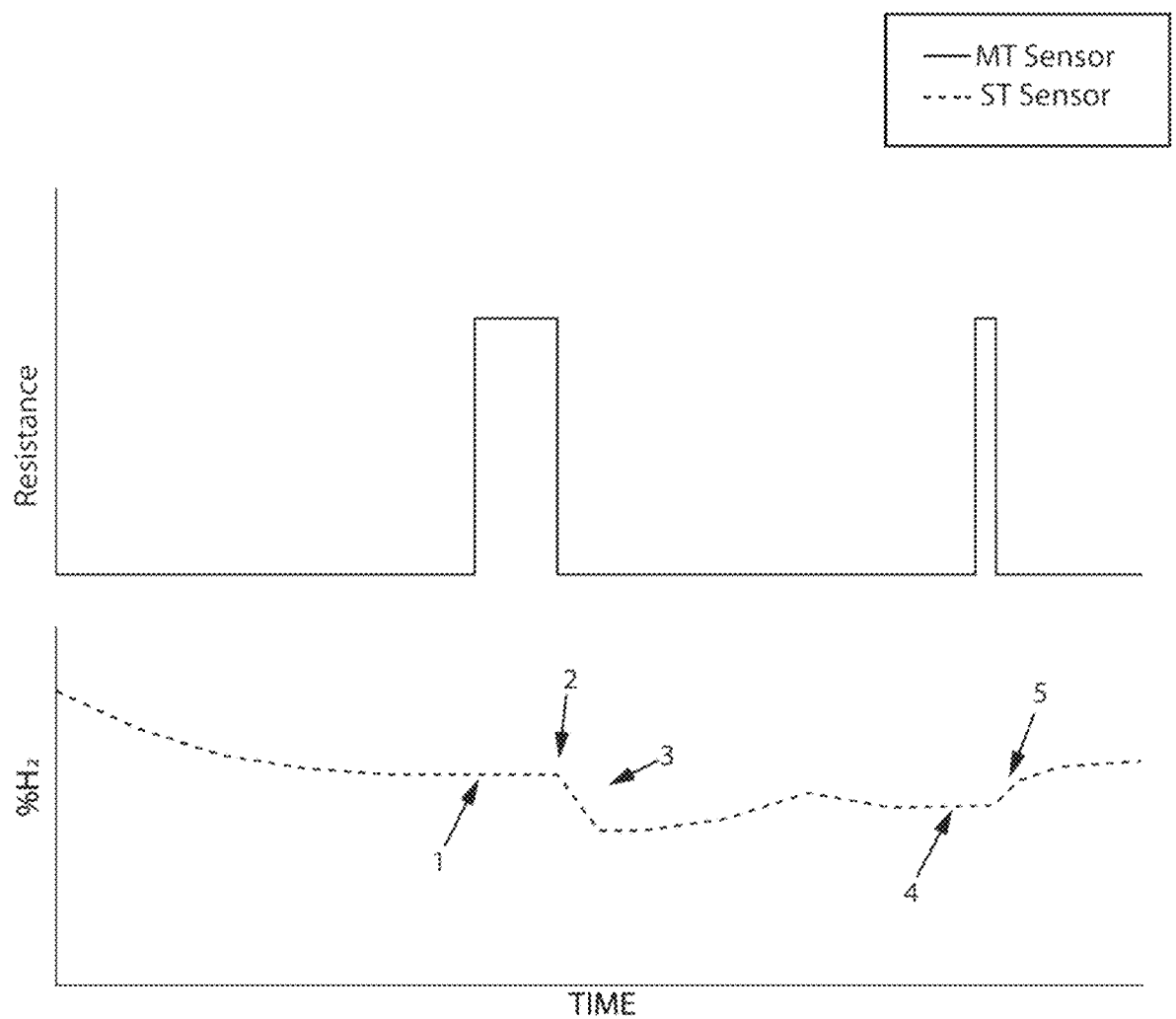
FIG. 3A shows the principle of operation of utilizing two gas sensors, wherein the multi-temp (MT) sensor (sensor used at two temperatures) can feed corrections forward to the single-temp (ST) sensor (sensor used at one temperature), and the ST sensor can feed stability information back to the MT sensor.

FIG. 3A shows an example of an output from a dual sensor embodiment with a first sensor (lower curve) showing the hydrogen concentration reading, and the second sensor (upper square wave) showing the results of a gas sensor employing the two-temperature method, which is used to calibrate the output of the first sensor. FIG. 3A shows where the ST sensor indicates the hydrogen is stable 1 and the MT sensor starts to cycle its temperature. When this temperature cycle completes, the ST Sensor shows the hydrogen is stable 2. A correction is blended 3 into the ST sensor's hydrogen reading. As the process repeats, the ST sensor indicates the hydrogen is stable 4, and the MT sensor starts to cycle its temperature again. If the ST sensor shows variability in hydrogen concentration 5, the MT sensor cancels its cycle and returns back to baseline.

Figure 3B:
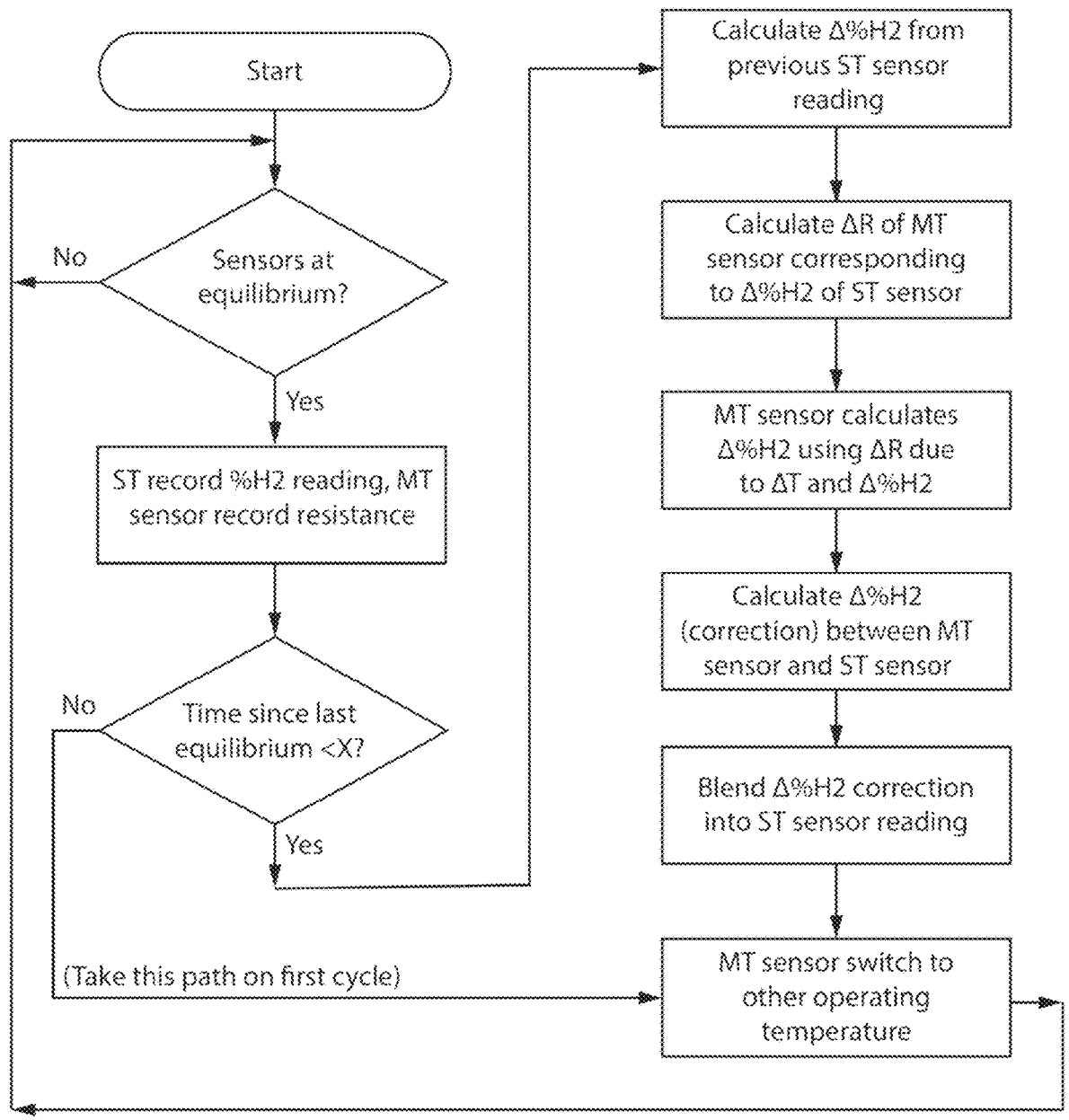
FIG. 3B shows a flow diagram of a method of measuring gas concentrations using a two-gas sensor system, wherein a first gas sensor is used at a single temperature, and a second gas sensor is used at two temperatures.

FIG. 3B shows a flow diagram demonstrating the process. When the process begins, the system determines whether the first and second gas sensors are at equilibrium. If not, then the system waits and continues to check whether equilibrium of both sensors has been reached. When the gas sensors reach equilibrium, the hydrogen concentration reading of the first gas sensor (the single temperature sensor) is recorded, while the resistance (or some other electrical property) of the second gas sensor (the two-temperature sensor) is recorded. The time from when the gas sensors were last in equilibrium is then determined. If the time since the last equilibrium for the gas sensors is greater than a predetermined time, then any previous readings are invalidated. The second gas sensor then switches to the other operating temperature (i.e., the second temperature if previously operating at the first temperature), and the process repeats with the step of determining whether the sensors are in equilibrium again. If there are valid readings from a full cycle (the second gas sensor has recorded readings from each of the two temperatures, and the first sensor has recorded the hydrogen reading associated with each of the second gas sensor's two temperatures), then the correction calculations can begin. First, the change in gas concentration (e.g., percent change in hydrogen concentration) from the previous reading of the first gas sensor is calculated. Then, the change in the electrical property (e.g. resistance) of the second gas sensor corresponding to the change in the gas concentration of the first sensor is calculated. The second gas sensor can then calculate the concentration of hydrogen associated with the most recent sensor temperature based on the change in resistance due to the change in temperature of the second gas sensor and the change in hydrogen recorded by the first gas sensor. This concentration of hydrogen calculated by the two-temperature is considered to more accurate than the hydrogen concentration calculated by the single-temperature sensor. The difference, if any, in the reading between the single-temp sensor and this reading is considered to be error in the single-temperature sensor. A correction factor to negate this error in the single-temperature sensor reading is calculated and blended into its hydrogen reading. The second gas sensor is switched to its other operating temperature and the process is repeated.

Figure 3C:
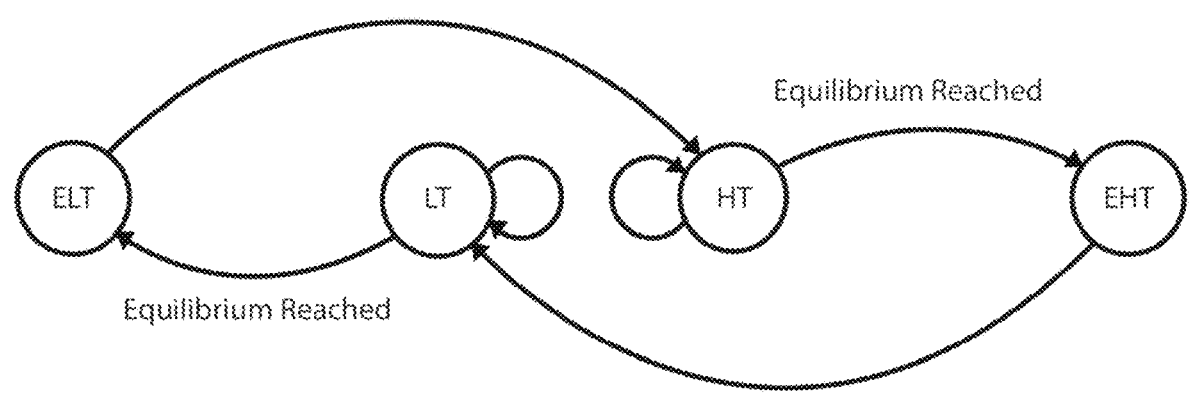
FIG. 3C shows the state machine of the dual-temperature sensor operation, where LT is "low temp state", ELT is "end of low temp state", HT is high temp state, and EHT is "end of high temp state."

As shown in FIG. 3C, as the second gas sensor reaches the end of a low temperature state (ELT) by determination of the equilibrium detector, it is transitioned to a high temperature state (HT). The end of the high temperature state (EHT) is determined again by the equilibrium detector, it is transitioned back to the low temperature state (LT), and the process repeats.

Figure 3D:
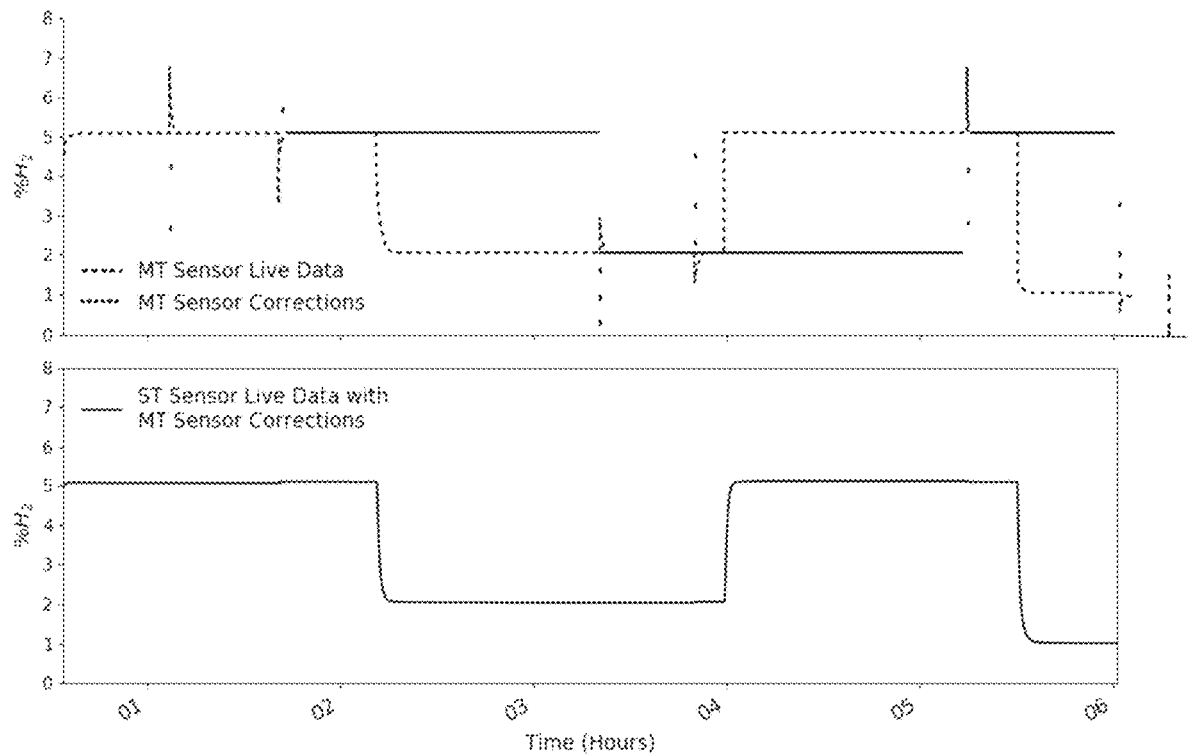
FIG. 3D shows an example of the dual-sensor operation.

FIG. 3D shows experimental data of this process. The figure contains three sets of data; the live hydrogen calculation of the two-temperature sensor (MT sensor reading), the hydrogen calculation using the multi-temp equation for the two-temperature sensor (calculated), and the live hydrogen calculation of the single-temperature sensor. The sensors were exposed to multiple hydrogen concentrations (5% $H_2/N_2$, 2% $H_2/N_2$, 5% $H_2/N_2$, then 1% $H_2/N_2$, all at a pressure of 1 atmosphere absolute). Looking at the live hydrogen calculation of the two-temperature sensor (MT sensor reading), spikes in the reading can be seen occasionally. These spikes are a result of the temperature transitions and can last several minutes to hours, depending on the response time of the sensor, the magnitude of the temperature change, and the hydrogen in the Pd lattice. The hydrogen calculation from the multi-temp equation for the two-temperature sensor (calculated) can be seen to update much less frequently than the live readings. The updates in the readings can only occur at the end of a temperature state of the two-temperature sensor, which can be seen in the figure using the aforementioned spikes as markers. As previously stated, these less frequent updates in hydrogen readings calculated from the multi-temp equation are considered accurate and do not degrade over time. To benefit from this, when these calculations are updated, they are fed forward to the live single-temp sensor reading (ST sensor reading). To allow the multi-temp equation to be used when the hydrogen concentration has been changed between temperatures (associated with the two-temperature sensor), the single-temperature sensor must record the change in hydrogen associated with the resistance measurements used in the multi-temp equation. This is described in more detail in the Single-Temperature Sensor Feedback Feature below.

Therefore, in some embodiments, a system and method of determining a target gas concentration in a fluid environment, comprises exposing a first gas sensor to the fluid environment, the first gas sensor having an electrical characteristic that varies as a function of the target gas concentration; exposing a second gas sensor to the fluid environment, the second gas sensor having an electrical characteristic that varies as a function of target gas concentration; alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time; monitoring the electrical characteristic of the second gas sensor during the second and fourth periods of time; and calculating the target gas concentration as a function of the electrical characteristic of the first gas sensor, wherein data from the second gas sensor is used to correct for baseline sensor drift of the first gas sensor. Preferably, the first gas sensor operates at a single temperature.

Second Sensor Using Repeating Thermal Waveform

The dual sensor feature described above can be combined with the repeating thermal waveform feature so that instead of the second sensor leveraging the two-temperature method, the second sensor can be in a constant state of transient response to a repeating thermal waveform such as a sinusoid, described previously. The second gas sensor passes corrections to the first gas sensor to keep the first gas sensor calibrated.

Single-Temp Sensor Feedback Feature

In some embodiments, with a single-temperature sensor, a dual-temperature sensor, or auto-calibrating sensors working together, changes in the environment can be accounted for. For example, the single-temperature sensor can show a change in hydrogen, if one does occur (e.g., by measuring it using resistance measurements and a calibration table), and by knowing that change, and quantifying that change, a multi-temperature correction can be calculated. For the multi-temperature equation to be valid, the assumption is the resistance measurement associated with the two temperatures corresponded to the same partial pressure of hydrogen. That is, if the partial pressure of hydrogen were to change between the two measurements, the hydrogen calculation using the equation would be incorrect. However, the single-temperature sensor, if present, can track the change in partial pressure of hydrogen during the period in which the dual-temperature sensor records the resistance at each of the two sensors. If any change was detected by the single-temperature sensor, the dual-temperature sensor can adjust one of the resistance measurements using its own calibration information. The "corrected" resistance value as adjusted to what the resistance would have been if the hydrogen concentration had not changed. This can only be known because the single-temperature sensor could track the change while the dual-temperature sensor was responding to the temperature transition and could not track the change. Therefore, the data from one of the sensors can be used in the other sensor, such as the first gas sensor reporting to the second gas sensor, a change in a partial pressure of hydrogen detected in the first gas sensor.

In other words, the two-sensor method can be used with the second sensor using the two-temperature method again, but if the partial pressure of hydrogen changes between the equilibrium state of the first period (temperature 1) of the second sensor and the equilibrium state of the third period (temperature 2) of the second sensor, then the first sensor can pass the magnitude of the change in partial pressure of hydrogen to the second sensor. This change can be compensated for using the sensitivity to hydrogen at one of the two temperatures of the second sensor, thus allowing the second sensor to still perform an auto-calibration in such a way that drift can be removed. (Information is fed back from the first, "live" sensor to the second sensor, allowing the second sensor to complete its auto-calibrations despite the change in environment.) This is mathematically described below:

Let, $$X_0 = X + C_{offset}$$

$$Y_0 = Y + C_{offset}$$

Where $X_0$ and $Y_0$ are the partial pressure of hydrogen readings of the ST sensor associated with the actual applied partial pressure of hydrogen values, X and Y, respectively, plus offset $C_{offset}$. Additionally, $X_0$ is the reading when MT sensor was at temperature T2, and $Y_0$ is the reading when the MT sensor was at temperature T1.

Let, $$R_{T2} = m_{T2}X + b_{T2}$$

$$R_{T1} = m_{T1}X + b_{T1}$$

Where $m_{T2}$ and $b_{T2}$ is the sensitivity and offset associated with the T2 isotherm, and $m_{T1}$ and $b_{T1}$ is the sensitivity and offset associated with the T1 isotherm. Further, let Rn be the measured resistance associated with partial pressure of hydrogen X at temperature T2, and let $R_{T1}$ be the unknown resistance associated with partial pressure of hydrogen X at temperature T1.

These can be combined to solve for X with the multi-temp equation below, $$R_{T2} - R_{T1} = m_{T2}X + b_{T2} - m_{T2}X - b_{T1}$$

$$X = \frac{R_{T2} - R_{T1} - (b_{T2} - b_{T1})}{m_{T2} - m_{T1}}$$

Finally, let, $$R' = m_{T1}Y + b_{T1}$$

Where R' is the actual measured resistance value the MT sensor took at temperature T1 when hydrogen concentration Y was applied.

Taking the difference in partial pressure of hydrogen readings in the ST sensor removes its offsets and results in the following equation:

$$X = \frac{R_{T2} - (R' + m_{T1}(X_0 - Y_0)) - (b_{T2} - b_{T1})}{m_{T2} - m_{T1}} \quad \text{a.}$$

The unknown X has been solved for with only known values. Other isotherms can also be used to solve it in a similar manner. Thus, the offsets cancel each other out.

Dual-Two-Temperature Sensors Feature

Figure 5:
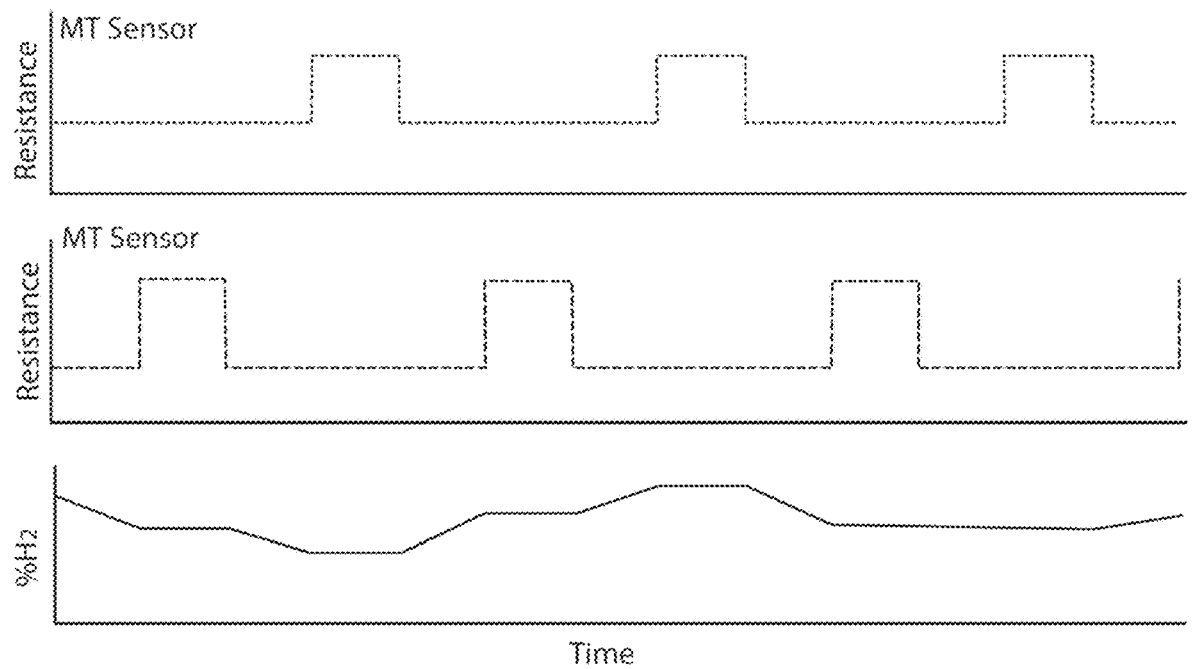
FIG. 5 shows the principle of two-sensor operation, wherein each sensor operates in MT mode and the temperature transitions are staggered such that one sensor can always be live.

In some embodiments, two sensors as described above can be used, but with both sensors using the two-temperature hydrogen measurement method. The periods of each sensor are staggered or offset such that the live sensor is always in the first period (temperature 1) or third period (temperature 2) while the other sensor is in a transition period (second or fourth) as shown in FIG. 5. The live sensor alternates between a first gas sensor (upper square wave) and a second gas sensor (lower square wave) as each transition between their states. So, when one sensor is going through the transient response, which is more difficult to calculate the varying hydrogen, the other sensor is at equilibrium. When the results of the two gas sensor readings are combined, a continuous gas concentration reading is shown (lower line).

Therefore, in some embodiments in which the first gas sensor operates at two temperatures, measuring gas concentrations further comprises alternately controlling the temperature of the first gas sensor between a first temperature and a second temperature while the first gas sensor is exposed to the gas, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor. In other words, when the first gas sensor is in its first period of time, the second gas sensor is in its second period of time (the transition period), and when the first gas sensor is in its second period of time (transition period), the second gas sensor is in its first period of time (or third period of time).

$2^{nd}$ Order Isotherms Feature

In some embodiments, the two-temperature method can be used, but instead of using a line to describe the resistance as a function of hydrogen at each isotherm, a second order polynomial is used. The offset from the two temperatures ($c_{T1}$ and $c_{T2}$) can be removed as mathematically described below where resistance at the two temperatures ($R_{T1}$ and $R_{T2}$) as a function of the partial pressure of hydrogen $\sqrt{H_2}$ given constant sensor temperatures $T_1$ or $T_2$ are a $2^{nd}$ order function given three respective coefficients $a_{T1}$ and $a_{T2}$, $b_{T1}$ and $b_{T2}$, and $C_{T1}$ and $c_{T2}$ for each respective temperature:

Let, $$R_{T1}(\sqrt{H_2}) = a_{T1}(\sqrt{H_2})^2 + b_{T1}(\sqrt{H_2}) + C_{T1} \quad \text{a.}$$

$$R_{T2}(\sqrt{H_2}) = a_{T2}(\sqrt{H_2})^2 + b_{T2}(\sqrt{H_2}) + C_{T2} \quad \text{b.}$$

Then, subtracting the equations linearly, $$R_{T2} - R_{T1} = a_{T2}(\sqrt{H_2})^2 + b_{T2}(\sqrt{H_2}) + C_{T2} - (a_{T1}(\sqrt{H_2})^2 + b_{T1}(\sqrt{H_2}) + c_{T1}) \quad \text{c.}$$

Solving for the partial pressure of hydrogen, $H_2$, there are two solutions:

$$\sqrt{H_2} = \frac{-(b_{T2} - b_{T1}) \pm \sqrt{(b_{T2} - b_{T1})^2 - 4(a_{T2} - a_{T1})(C_{T2} - C_{T1}) - (R_{T2} - R_{T1})}}{2(a_{T2} - a_{T1})} \quad \text{i.}$$

The solution nearest the operating region of the isotherms is shown below (the other solution results in negative or extremely large partial pressure of hydrogen calculations, regardless of isotherm concavity):

$$\sqrt{H_2} = \frac{-(b_{T2} - b_{T1}) - \sqrt{(b_{T2} - b_{T1})^2 - 4(a_{T2} - a_{T1})(C_{T2} - C_{T1}) - (R_{T2} - R_{T1})}}{2(a_{T2} - a_{T1})} \quad \text{i.}$$

Piecewise Linear Isotherms Feature

The sensitivity of the system refers to how effectively the resistance (or other electrical characteristic) of the gas sensor changes with hydrogen content. The sensitivity of the sensor is not necessarily constant across a full range of hydrogen content. When exposed to different hydrogen content, the gas sensor may have different sensitivities. As such, it is beneficial to account for the changing sensitivities based on the hydrogen content of the environment tested.

Factors that affect the sensitivity of the gas sensor include the composition of the sensor (e.g. the palladium/nickel ratio) and the temperature of the gas sensor. The more palladium in the sensor, the more the resistance changes with hydrogen; thereby, increasing the sensitivity of the gas sensor. In addition, the lower the temperature, the more sensitive the gas sensor becomes. The palladium content and operating temperature can be determined based on the performance requirements of the product application.

The two-temperature method can be used by using a sensitivity and intercept of the two isotherms (resistance as a function of partial pressure of hydrogen at a given temperature) based on the partial pressure of hydrogen the sensor is measuring, given the best information available. That is, for concentrations between $X_0$ and $X_1$, use sensitivities and intercepts $A_0$, for concentrations between $X_1$ and $X_2$, use sensitivities and intercepts $A_1$, etc., across the full range of hydrogen.

Figure 6A:
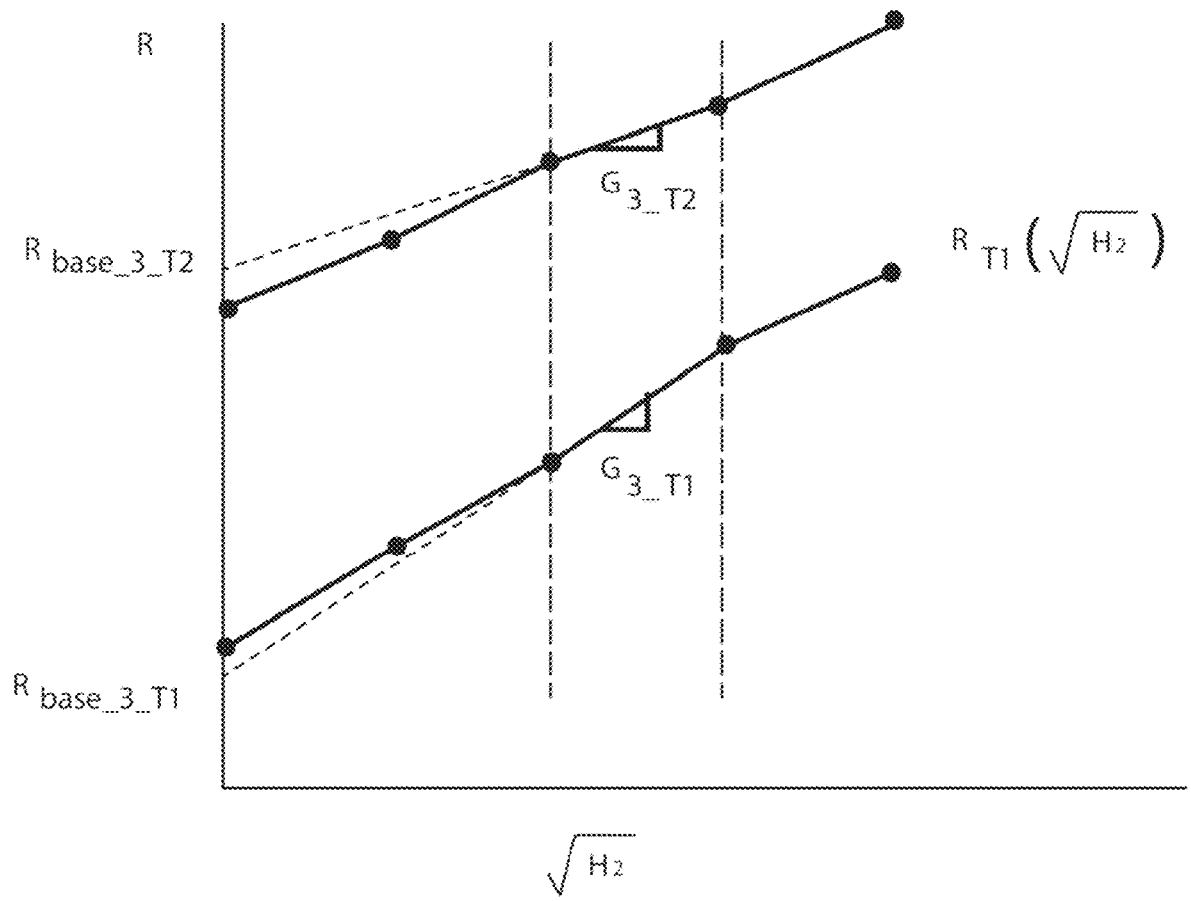
FIG. 6A shows the two isotherms associated with a gas sensor that operates at two temperatures, wherein each isotherm is defined by a piecewise calibration.
Figure 6B:
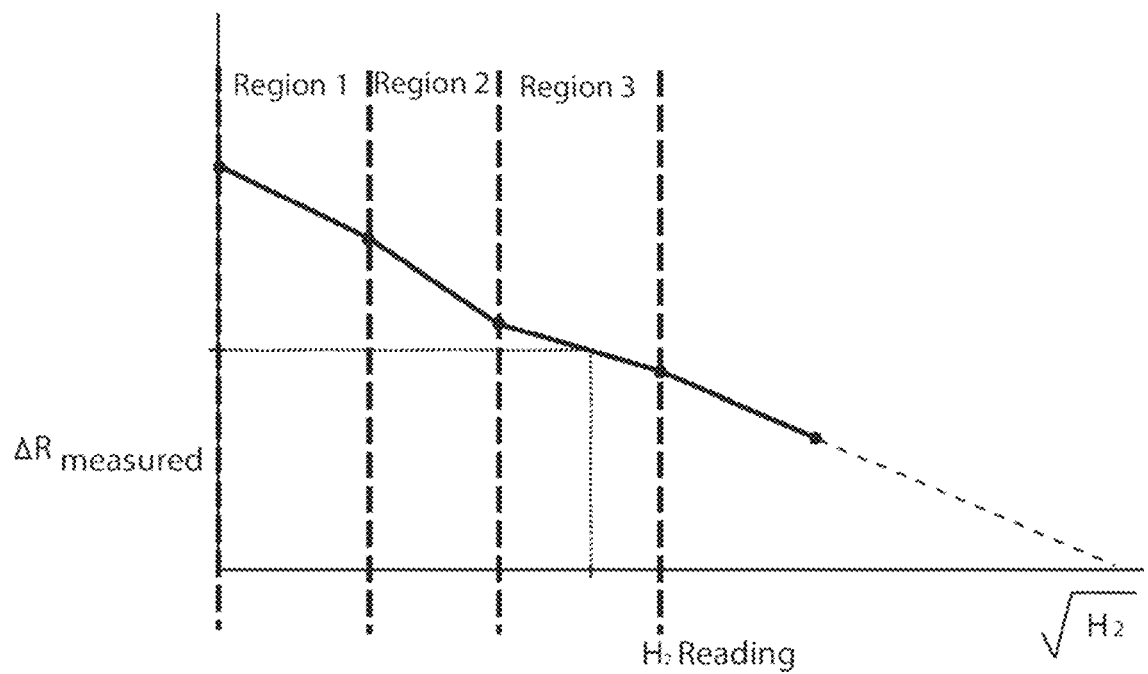
FIG. 6B shows the difference of the two isotherms shown in FIG. 6A, and how a delta-R measurement can be looked up to generate a hydrogen reading.
Figure 6C:
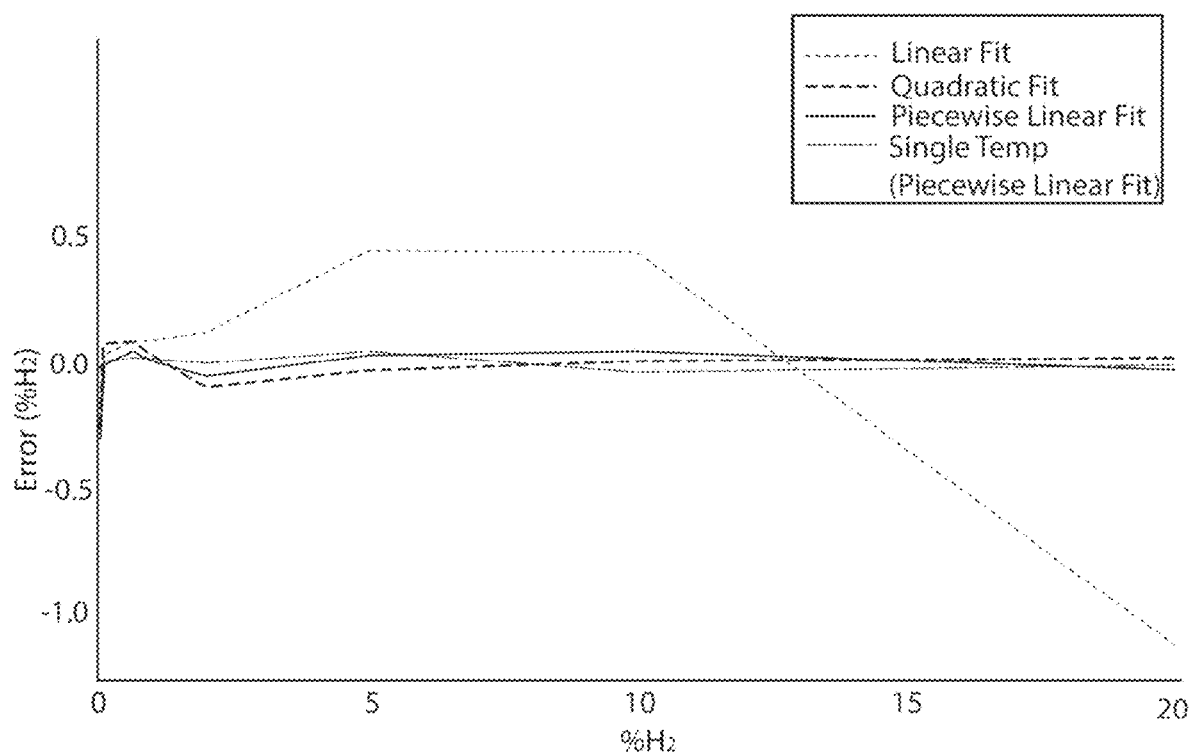
FIG. 6C shows a comparison of hydrogen measurement performance on the same set of data.

With reference to FIGS. 6A-6C, if the ΔR ($R_{T2}-R_{T1}$) falls in the range of ΔR's in region 3:

$$R_{T1} = G_{3\_T1} \cdot \sqrt{H_2} + R_{base\_2_{T1}}$$

$$R_{T2} = G_{3\_T2} \cdot \sqrt{H_2} + R_{base\_2_{T2}}$$

$$\sqrt{H_2} = \frac{(R_{T2} - R_{T1}) - (R_{base\_3_{T2}} - R_{base\_3_{T1}})}{G_{3\_T2} - G_{3\_T1}}$$

The standard multi-temp equation shown above still applies, but the values $G_{3\_T1}$, $G_{3\_T2}$, $R_{base\_3T1}$, and $R_{base\_3T2}$ all correspond to the specific piece or region in the piecewise table. If the ΔR ($R_{T2}-R_{T1}$) fell in a different region, then the aforementioned variables associated with that region would be used. These variables are determined in calibration.

To determine which region the ΔR ($R_{T2}-R_{T1}$) falls in, the difference of the isotherms can be taken as shown in FIG. 6B.

FIG. 6C shows a comparison of different methods of interpolating the isotherms, as well as a comparison to a single-temp sensor's calibration table using a piecewise linear fit. It can be seen that using a standard linear regression on the isotherms can result in much larger error in the model compared to using a piecewise linear (like shown in FIG. 6B) or quadratic regression ($2^{nd}$ order polynomial regression)

Piecewise $2^{nd}$ Order Isotherms Feature

Another feature of the present invention is to use the $2^{nd}$ order polynomial isotherms but use a different set of coefficients for different regions of hydrogen, as described in the piecewise linear isotherms.

Generic Non-Linear Calibration Feature

The isotherm can be described as an $n^{th}$ order polynomial, a power function, or similar nonlinear function. The coefficients to these isotherms can be generically determined for a wafer as a function of base resistance and sensitivity. During calibration, the nonlinear isotherm function can be calibrated using two points (known partial pressure of hydrogen and resistance), adjusting the coefficients to fit the two points using a linear transformation.

Multi-Temperature Limiting Transitions Feature

Two-temperature operation requires a significant temperature difference between a first temperature and a second temperature, such that the transition periods between the temperature states induces an undesirable transient response of the hydrogen sensor that typically results in reduced measurement capabilities, or at worst, no measurement capabilities. Alternatively, n-number of temperature states can be added between temperature A and temperature A+N such that only small increases or decreases in temperature occur at a time, reducing the magnitude of the undesirable transient response. That is, the sensor may be at temperature A for a first period, then transitions to temperature A+1 for a second period, remain at temperature A+1 for a third period, transition to temperature A+2 for a fourth period, transition to temperature A+N for a n–$1^{th}$ period, and remain at temperature A+N for an $n^{th}$ period. The sensor can return to temperature A in the reverse order. The assumption is hydrogen can be calculated live at each of the temperature states with the highest accuracy and may be calculated with potentially reduced accuracy during the transition states. The measurements from temperature A and A+N states are used in the two-temperature formula to calculate hydrogen with the offset removed.

To reduce the undesirable transient response, the step from one temperature to the next temperature can be made sufficiently small that any undesirable transient response is very small and short lived to the point that there is virtually no interrupted hydrogen reading.

By way of example only, a major step from a first temperature to a second temperature may be about 20 degrees C. For the gas sensor to take reliable measurements, equilibrium must be reached, which could take 30 minutes. Therefore, 30 minutes must pass before the gas sensor is live again. On the other hand, if instead of taking a full major step of 20 degrees, if a one degree minor step is used, lesser time is required to reach equilibrium, and the gas sensor can be live again after 30 seconds rather than 30 minutes. Then the gas sensor can perform measurements at multiple spaced out minor steps to approach the 20 degree total major step, and utilize the multi-temperature equations to calculate the hydrogen concentrations at each minor step. This technique effectively reduces the amount of time measurements cannot be taken with the system at equilibrium, without having to rely on transient responses during the transition period.

Heater Power Correction Feature

Given a constant partial pressure of hydrogen and operating temperature of the sensor in an environment without interference gases, the resistance should remain constant (except for small drifts due to instability). However, as the environment thermal load changes on the die (due to environment temperature, flow rate, etc.), the sensor resistance changes. This change in resistance can be compensated using the measured power used to maintain the sensor die temperature. The correction assumes the resistance adjustment is proportional to the heater power measurement. The compensated resistance is equal to the measurement resistance plus the adjustment, as described below:

$$R_{comp} = R_{meas} - R_{adj} \qquad \text{ii.}$$

Where, $$R_{adj} = \alpha P \qquad \text{iii.}$$

The heater power coefficient, α, when used to compensate the measured resistance effectively normalizes the resistance to that of no power.

Temperature Dependent Heater Power Correction Feature

The heater power correction where the heater power coefficient is also a function of operating temperature.

Hydrogen Dependent Heater Power Correction Feature

In the heater power correction method, the heater power coefficient may also be a function of the partial pressure of hydrogen.

Heater Power to Calculate Environment Temperature Feature

In the two-temperature method, the power required to heat the die at the equilibrium states of the first period (temperature 1) and the third period (temperature 2) can be measured and recorded. Assuming the environment temperature and thermal loading on the die is constant, the temperature of the environment can be calculated using the linear function described below:

Let, $P_{T_1}$ be the die heater power at temperature $T_1$     a.

$P_{T_2}$ be the die heater power at temperature $T_2$     b.

$T_{env}$ be the unknown environment temperature, below $T_1$ and $T_2$     c.

Then, $$m = \frac{T_2 - T_1}{P_{T_2} - P_{T_1}} \qquad \text{d.}$$

Using the $T_1$ information to solve, $$T_{env} = T_1 - m \cdot P_{T_1} \qquad \text{e.}$$

Or, full form, $$T_{env} = T_1 - \frac{T_2 - T_1}{P_{T_2} - R_{T_1}} \cdot P_{T_1} \qquad \text{f.}$$

The foregoing description of the preferred embodiment and features of the invention has been presented for the purposes of illustration and description. It is not intended to be exhaustive or to limit the invention to the precise form disclosed. Many modifications, variations, and combinations are possible in light of the above teaching. It is intended that the scope of the invention not be limited by this detailed description, but by the claims and the equivalents to the claims appended hereto.

What is claimed is:

1. A method of determining a target gas concentration of a target gas in a fluid environment, the method comprising the steps of:
   (a) exposing a gas sensor to the fluid environment, the gas sensor having an electrical characteristic that varies as a function of the target gas concentration;
   (b) during step (a) modulating the temperature of the gas sensor, wherein the modulation is in a form of a repeating thermal waveform that induces a magnitude-frequency response in the electrical characteristics;
   (c) monitoring the electrical characteristics during step (b); and
   (d) calculating the target gas concentration as a function of the magnitude-frequency response of the electrical characteristics of the gas sensor, wherein the repeating thermal waveform is generated by a superposition of multiple sine waves, wherein each sine wave has a corresponding magnitude-frequency response calibration table.

2. The method of claim 1, wherein the calibration table is generated by associating the target gas concentration with the magnitude-frequency response measured using a Short Time Fourier Transform.

3. The method of claim 2, further comprising correcting a shift in the magnitude-frequency response by applying a known partial pressure of the target gas to the sensor, allowing the sensor to generate a second magnitude-frequency response, and applying a correction to the calibration table based on the second magnitude-frequency response.

4. The method of claim 2, further comprising applying a correction to the calibration table by:
   (a) allowing the sensor to generate a second magnitude-frequency response;
   (b) changing an operating mode of the gas sensor to operate at two temperatures;
   (c) alternately controlling the temperature of the gas sensor between a first temperature and a second temperature while the gas sensor is exposed to the gas, wherein the temperature of the gas sensor remains at the first temperature over a first period of time, transitions from the first temperature to the second temperature over a second period of time, remains at the second temperature over a third period of time, and transitions from the second temperature to a third temperature over a fourth period of time;
   (d) monitoring the electrical characteristic of the gas sensor during the second and fourth periods of time;
   (e) calculating the target gas concentration as a function of the electrical characteristics; and
   (f) calculating the correction based on the second magnitude-frequency response and the calculated target gas concentration.

5. The method of claim 1, wherein the multiple sine waves comprise a first set of sine waves having a first set of frequencies, and a second set of sine waves having a second set of frequencies, wherein the first set of frequencies is lower than the second set of frequencies, and wherein calculation of the target gas concentration is based on the magnitude-frequency response of one of the first set of frequencies or the second set of frequencies.

6. A method of determining a target gas concentration of a target gas in a fluid environment, the method comprising the steps of:
   (a) exposing a gas sensor to the fluid environment, the gas sensor having an electrical characteristic that varies as a function of the target gas concentration;
   (b) during step (a) modulating the temperature of the gas sensor, wherein the modulation is in a form of a repeating thermal waveform that induces a phase-frequency response in the electrical characteristics;
   (c) monitoring the electrical characteristics during step (b); and
   (d) calculating the target gas concentration as a function of the phase-frequency response of the electrical characteristics of the gas sensor, wherein the repeating thermal waveform is generated by a superposition of multiple sine waves, wherein each sine wave has a corresponding phase-frequency response calibration table.

7. The method of claim 6, wherein the calibration table is generated by associating the target gas concentration with the phase-frequency response measured using a Short Time Fourier Transform.

8. The method of claim 7, further comprising correcting a shift in the phase-frequency response by applying a known partial pressure of the target gas to the sensor, allowing the sensor to generate a second phase-frequency response, and applying a correction to the calibration table based on the second phase-frequency response.

9. The method of claim 7, further comprising applying a correction to the calibration table by:
   (a) allowing the sensor to generate a second phase-frequency response;
   (b) changing an operating mode of the gas sensor to operate at two temperatures;
   (c) alternately controlling the temperature of the gas sensor between a first temperature and a second temperature while the gas sensor is exposed to the gas, wherein the temperature of the gas sensor remains at the first temperature over a first period of time, transitions from the first temperature to the second temperature over a second period of time, remains at the second temperature over a third period of time, and transitions from the second temperature to a third temperature over a fourth period of time;
   (d) monitoring the electrical characteristic of the gas sensor during the second and fourth periods of time;

(e) calculating the target gas concentration as a function of the electrical characteristics; and (f) calculating the correction based on the second phase-frequency response and the calculated target gas concentration.

10. The method of claim 6, wherein the multiple sine waves comprise a first set of sine waves having a first set of frequencies, and a second set of sine waves having a second set of frequencies, wherein the first set of frequencies is lower than the second set of frequencies, and wherein calculation of the target gas concentration is based on the phase-frequency response of one of the first set of frequencies or the second set of frequencies.

11. A method of determining a target gas concentration of a target gas in a fluid environment, comprising:
  (a) exposing a first gas sensor to the fluid environment, the first gas sensor having an electrical characteristic that varies as a function of the target gas concentration, and monitoring electrical characteristics of the first gas sensor;
  (b) exposing a second gas sensor to the fluid environment, the second gas sensor having an electrical characteristic that varies as a function of the target gas concentration;
  (c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
  (d) monitoring the electrical characteristic of the second gas sensor during the second and fourth periods of time; and
  (e) calculating the target gas concentration as a function of the electrical characteristic of the first gas sensor, wherein data from the second gas sensor is used to correct for baseline sensor drift of the first gas sensor, wherein the third temperature of the second gas sensor is equal to the first temperature.

12. The method of claim 11, wherein the first gas sensor operates at a single temperature.

13. The method of claim 12, wherein the second gas sensor is in a constant state of system response to a repeating thermal waveform.

14. The method of claim 13, further comprising the first gas sensor reporting to the second gas sensor, a change in a partial pressure of the target gas detected in the first gas sensor.

15. A method of determining a target gas concentration of a target gas in a fluid environment, comprising:
  (a) exposing a first gas sensor to the fluid environment, the first gas sensor having an electrical characteristic that varies as a function of the target gas concentration, and monitoring electrical characteristics of the first gas sensor;
  (b) exposing a second gas sensor to the fluid environment, the second gas sensor having an electrical characteristic that varies as a function of the target gas concentration;
  (c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
  (d) monitoring the electrical characteristic of the second gas sensor during the second and fourth periods of time; and
  (e) calculating the target gas concentration as a function of the electrical characteristic of the first gas sensor, wherein data from the second gas sensor is used to correct for baseline sensor drift of the first gas sensor, wherein the third temperature of the second gas sensor is equal to the first temperature, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor.

16. A method of determining a target gas concentration of a target gas in a fluid environment, comprising:
  (a) exposing a first gas sensor to the fluid environment, the first gas sensor having an electrical characteristic that varies as a function of the target gas concentration, and monitoring electrical characteristics of the first gas sensor;
  (b) exposing a second gas sensor to the fluid environment, the second gas sensor having an electrical characteristic that varies as a function of the target gas concentration;
  (c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
  (d) monitoring the electrical characteristic of the second gas sensor during the second and fourth periods of time; and
  (e) calculating the target gas concentration as a function of the electrical characteristic of the first gas sensor, wherein data from the second gas sensor is used to correct for baseline sensor drift of the first gas sensor, wherein the third temperature of the second gas sensor is equal to the first temperature, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor, wherein the transition from the first temperature to the second temperature of the first gas sensor comprises a plurality of stepped increases of the temperature from the first temperature to the second temperature of the first gas sensor.

17. A method of determining a target gas concentration of a target gas in a fluid environment, comprising:
(a) exposing a first gas sensor to the fluid environment, the first gas sensor having an electrical characteristic that varies as a function of the target gas concentration, and monitoring electrical characteristics of the first gas sensor;
(b) exposing a second gas sensor to the fluid environment, the second gas sensor having an electrical characteristic that varies as a function of the target gas concentration;
(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
(d) monitoring the electrical characteristic of the second gas sensor during the second and fourth periods of time;
(e) calculating the target gas concentration as a function of the electrical characteristic of the first gas sensor, wherein data from the second gas sensor is used to correct for baseline sensor drift of the first gas sensor, wherein the third temperature of the second gas sensor is equal to the first temperature, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor, wherein the transition from the first temperature to the second temperature of the first gas sensor comprises a plurality of stepped increases of the temperature from the first temperature to the second temperature of the first gas sensor; and
(f) calculating the target gas concentration as a function of the electrical characteristics of the first gas sensor at each of the plurality of stepped increases of the temperature.

18. The method of claim 11, wherein the transition from the first temperature to the second temperature of the second gas sensor comprises a plurality of stepped increases of the temperature from the first temperature to the second temperature.

19. A method of determining a target gas concentration of a target gas in a fluid environment, comprising:
(a) exposing a first gas sensor to the fluid environment, the first gas sensor having an electrical characteristic that varies as a function of the target gas concentration, and monitoring electrical characteristics of the first gas sensor;
(b) exposing a second gas sensor to the fluid environment, the second gas sensor having an electrical characteristic that varies as a function of the target gas concentration;
(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
(d) monitoring the electrical characteristic of the second gas sensor during the second and fourth periods of time; and
(e) calculating the target gas concentration as a function of the electrical characteristic of the first gas sensor, wherein data from the second gas sensor is used to correct for baseline sensor drift of the first gas sensor, further comprising the step of:
(f) determining whether the first gas sensor and the second gas sensor each reach an equilibrium state,
(g) when the first gas sensor and the second gas sensor reach their respective equilibrium state, determining a prior time when the first gas sensor and the second gas sensor reached their respective equilibrium state, and
(h) if the prior time is greater than a predetermined time, then invalidating the electrical characteristics of the first gas sensor and the second gas sensor measured at the prior time.

20. The method of claim 19, wherein the first gas sensor operates at a single temperature.

21. The method of claim 20, wherein the second gas sensor is in a constant state of system response to a repeating thermal waveform.

22. A method of determining a target gas concentration of a target gas in a fluid environment, comprising:
(a) exposing a first gas sensor to the fluid environment, the first gas sensor having an electrical characteristic that varies as a function of the target gas concentration, and monitoring electrical characteristics of the first gas sensor;
(b) exposing a second gas sensor to the fluid environment, the second gas sensor having an electrical characteristic that varies as a function of the target gas concentration;

(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;

(d) monitoring the electrical characteristic of the second gas sensor during the second and fourth periods of time;

(f) determining whether the first gas sensor and the second gas sensor each reach an equilibrium state;

(g) when the first gas sensor and the second gas sensor reach their respective equilibrium state, determining a prior time when the first gas sensor and the second gas sensor reached their respective equilibrium state; and (h) if the prior time is greater than a predetermined time, then invalidating the electrical characteristics of the first gas sensor and the second gas sensor measured at the prior time, wherein the first gas sensor operates at a single temperature, wherein the second gas sensor is in a constant state of system response to a repeating thermal waveform, wherein the first gas sensor reports to the second gas sensor, a change in a partial pressure of the target gas detected in the first gas sensor.

23. A method of determining a target gas concentration of a target gas in a fluid environment, comprising:

(a) exposing a first gas sensor to the fluid environment, the first gas sensor having an electrical characteristic that varies as a function of the target gas concentration, and monitoring electrical characteristics of the first gas sensor;

(b) exposing a second gas sensor to the fluid environment, the second gas sensor having an electrical characteristic that varies as a function of the target gas concentration;

(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;

(d) monitoring the electrical characteristic of the second gas sensor during the second and fourth periods of time;

(f) determining whether the first gas sensor and the second gas sensor each reach an equilibrium state;

(g) when the first gas sensor and the second gas sensor reach their respective equilibrium state, determining a prior time when the first gas sensor and the second gas sensor reached their respective equilibrium state;

(h) if the prior time is greater than a predetermined time, then invalidating the electrical characteristics of the first gas sensor and the second gas sensor measured at the prior time; and (i) calculating the target gas concentration as a function of the electrical characteristic of the first gas sensor, wherein data from the second gas sensor is used to correct for baseline sensor drift of the first gas sensor, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor.

24. A method of determining a target gas concentration of a target gas in a fluid environment, comprising:

(a) exposing a first gas sensor to the fluid environment, the first gas sensor having an electrical characteristic that varies as a function of the target gas concentration, and monitoring electrical characteristics of the first gas sensor;

(b) exposing a second gas sensor to the fluid environment, the second gas sensor having an electrical characteristic that varies as a function of the target gas concentration;

(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;

(d) monitoring the electrical characteristic of the second gas sensor during the second and fourth periods of time;

(e) determining whether the first gas sensor and the second gas sensor each reach an equilibrium state;

(f) when the first gas sensor and the second gas sensor reach their respective equilibrium state, determining a prior time when the first gas sensor and the second gas sensor reached their respective equilibrium state;

(h) if the prior time is greater than a predetermined time, then invalidating the electrical characteristics of the first gas sensor and the second gas sensor measured at the prior time;

(i) calculating the target gas concentration as a function of the electrical characteristic of the first gas sensor, wherein data from the second gas sensor is used to correct for baseline sensor drift of the first gas sensor, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time; wherein the temperatures of the first gas sensor and the second gas sensor are staggered such that when the first gas sensor is in the first period of time or third period of time of the first gas sensor, the second gas sensor is in the second period of time or the fourth period of time of the second gas sensor, wherein the transition from the first temperature to the second temperature of the first gas sensor comprises a plurality of stepped increases of the temperature from the first temperature to the second temperature of the first gas sensor.

25. A method of determining a target gas concentration of a target gas in a fluid environment, comprising:
(a) exposing a first gas sensor to the fluid environment, the first gas sensor having an electrical characteristic that varies as a function of the target gas concentration, and monitoring electrical characteristics of the first gas sensor;
(b) exposing a second gas sensor to the fluid environment, the second gas sensor having an electrical characteristic that varies as a function of the target gas concentration;
(c) alternately controlling the temperature of the second gas sensor between a first temperature and a second temperature while the second gas sensor is exposed to the fluid environment, wherein the temperature of the second gas sensor remains at the first temperature over a first period of time, transitions from the first temperature to the second temperature over a second period of time, remains at the second temperature over a third period of time, and transitions from the second temperature to a third temperature over a fourth period of time;
(d) monitoring the electrical characteristic of the second gas sensor during the second and fourth periods of time;
(f) determining whether the first gas sensor and the second gas sensor each reach an equilibrium state;
(g) when the first gas sensor and the second gas sensor reach their respective equilibrium state, determining a prior time when the first gas sensor and the second gas sensor reached their respective equilibrium state;
(h) if the prior time is greater than a predetermined time, then invalidating the electrical characteristics of the first gas sensor and the second gas sensor measured at the prior time; and
(i) calculating the target gas concentration as a function of the electrical characteristic of the first gas sensor, wherein data from the second gas sensor is used to correct for baseline sensor drift of the first gas sensor, wherein the first gas sensor operates at two temperatures, and further comprising alternately controlling the temperature of the first gas sensor between a first temperature and a second temperature while the first gas sensor is exposed to the fluid environment, wherein the temperature of the first gas sensor remains at the first temperature over a first period of time, transitions from the first temperature to the second temperature over a second period of time, remains at the second temperature over a third period of time, and transitions from the second temperature to a third temperature over a fourth period of time, wherein the temperatures of the first gas sensor and the second gas sensor are staggered such that when the first gas sensor is in the first period of time or third period of time of the first gas sensor, the second gas sensor is in the second period of time or the fourth period of time of the second gas sensor, wherein the transition from the first temperature to the second temperature of the first gas sensor comprises a plurality of stepped increases of the temperature from the first temperature to the second temperature of the first gas sensor; and
(i) calculating the target gas concentration as a function of the electrical characteristics of the first gas sensor at each of the plurality of stepped increases of the temperature.

26. The method of claim 19, wherein the transition from the first temperature to the second temperature of the second gas sensor comprises a plurality of stepped increases of the temperature from the first temperature to the second temperature.

* * * * *